US012575882B2

(12) United States Patent  
Mukai et al.

(10) Patent No.: US 12,575,882 B2  
(45) Date of Patent: Mar. 17, 2026

(54) PUNCTURING DEVICE

(71) Applicant: KANEKA CORPORATION, Osaka (JP)

(72) Inventors: Yuki Mukai, Okaya (JP); Miho Kobayashi, Okaya (JP)

(73) Assignee: KANEKA CORPORATION, Osaka (JP)

( * ) Notice: Subject to any disclaimer, the term of this patent is extended or adjusted under 35 U.S.C. 154(b) by 315 days.

(21) Appl. No.: 18/277,828

(22) PCT Filed: Feb. 1, 2022

(86) PCT No.: PCT/JP2022/003880  
§ 371 (c)(1),  
(2) Date: Aug. 18, 2023

(87) PCT Pub. No.: WO2022/176604  
PCT Pub. Date: Aug. 25, 2022

(65) Prior Publication Data  
US 2024/0130781 A1 Apr. 25, 2024  
US 2024/0225725 A9 Jul. 11, 2024

(30) Foreign Application Priority Data

Feb. 22, 2021 (JP) ................................ 2021-025788

(51) Int. Cl.  
*A61B 18/14* (2006.01)  
*A61B 17/00* (2006.01)  
(Continued)

(52) U.S. Cl.  
CPC .................... *A61B 18/1492* (2013.01); *A61B 2017/00247* (2013.01); *A61B 17/3478* (2013.01);  
(Continued)

(58) Field of Classification Search  
CPC ...... A61B 18/1492; A61B 2018/00351; A61B 2017/00247; A61B 17/3417; A61B 17/3478  
See application file for complete search history.

(56) References Cited

U.S. PATENT DOCUMENTS 8,794,629 B1 8/2014 Humphreys, Jr.  
2004/0143261 A1 7/2004 Hartley et al.  
(Continued)

FOREIGN PATENT DOCUMENTS

CN 116457046 A 7/2023  
JP 2012-135338 A 7/2012  
(Continued)

OTHER PUBLICATIONS

International Search Report (PCT/ISA/210), issued in PCT/JP2022/003880, mailed Mar. 29, 2022.

*Primary Examiner* — Sean W Collins  
(74) *Attorney, Agent, or Firm* — Birch, Stewart, Kolasch & Birch, LLP

(57) ABSTRACT

A puncturing device comprising: a resin tube having a distal end and a proximal end, and extending in a longitudinal direction; a metal tube disposed in a lumen of the resin tube; a metal member disposed at a distal end portion of the metal tube; and a metal tip disposed at a distal end portion of the metal member, wherein a flow path is present between an inner surface of the resin tube and an outer surface of the metal member and is in communication with a lumen of the metal tube, the resin tube further includes an opening portion through which the flow path and outside of the resin tube are in communication with each other, and the opening portion is present on a distal side relative to a distal end of the metal tube and on a proximal side relative to the proximal end of the metal tip.

17 Claims, 11 Drawing Sheets

(51) Int. Cl.

| | |
|---|---|
| *A61B 17/34* | (2006.01) |
| *A61B 18/00* | (2006.01) |
| *A61M 25/00* | (2006.01) |
| *A61M 25/01* | (2006.01) |

(52) U.S. Cl.

CPC ................. *A61B 2018/0038* (2013.01); *A61B 2018/00601* (2013.01); *A61M 25/0082* (2013.01); *A61M 2025/0166* (2013.01)

(56) References Cited

U.S. PATENT DOCUMENTS

| | | | |
|---|---|---|---|
| 2004/0143262 | A1 | 7/2004 | Visram et al. |
| 2005/0065507 | A1 | 3/2005 | Hartley et al. |
| 2005/0159738 | A1 | 7/2005 | Visram et al. |
| 2006/0142756 | A1 | 6/2006 | Davies et al. |
| 2007/0066975 | A1 | 3/2007 | Wong et al. |
| 2007/0123964 | A1 | 5/2007 | Davies et al. |
| 2007/0185522 | A1 | 8/2007 | Davies et al. |
| 2008/0086120 | A1 | 4/2008 | Mirza et al. |
| 2008/0208121 | A1 | 8/2008 | Youssef et al. |
| 2009/0163913 | A1* | 6/2009 | Wang ................. A61B 18/1492 606/41 |
| 2011/0118735 | A1 | 5/2011 | Abou-Marie et al. |
| 2011/0224666 | A1 | 9/2011 | Davies et al. |
| 2012/0046657 | A1 | 2/2012 | Biadillah et al. |
| 2012/0165809 | A1* | 6/2012 | Christian ........... A61B 18/1492 606/41 |
| 2012/0215213 | A1 | 8/2012 | Juzkiw et al. |
| 2012/0232546 | A1 | 9/2012 | Mirza et al. |
| 2014/0039315 | A1 | 2/2014 | Davies et al. |
| 2014/0039484 | A1 | 2/2014 | Leung |
| 2014/0100560 | A1 | 4/2014 | Biadillah et al. |
| 2014/0100561 | A1 | 4/2014 | Biadillah et al. |
| 2014/0206987 | A1 | 7/2014 | Urbanski et al. |
| 2015/0216620 | A1* | 8/2015 | Davies .............. A61M 25/0127 606/41 |
| 2015/0374431 | A1 | 12/2015 | Davies et al. |
| 2016/0000501 | A1 | 1/2016 | Davies et al. |
| 2016/0038216 | A1 | 2/2016 | Woo et al. |
| 2016/0066989 | A1 | 3/2016 | Davies et al. |
| 2016/0262795 | A1 | 9/2016 | Urbanski et al. |
| 2016/0374751 | A1 | 12/2016 | Davies et al. |
| 2017/0071667 | A1 | 3/2017 | Leung et al. |
| 2017/0189113 | A1 | 7/2017 | Urbanski et al. |
| 2017/0224411 | A1 | 8/2017 | Onuki et al. |
| 2019/0216528 | A1 | 7/2019 | Woo et al. |
| 2019/0231424 | A1* | 8/2019 | Davies .............. A61B 18/1492 |
| 2019/0239924 | A1 | 8/2019 | Urbanski et al. |
| 2019/0274754 | A1 | 9/2019 | Davies et al. |
| 2019/0374281 | A1 | 12/2019 | Davies et al. |
| 2020/0345410 | A1 | 11/2020 | Davies et al. |
| 2021/0000536 | A1 | 1/2021 | Davies et al. |
| 2021/0121227 | A1 | 4/2021 | Davies et al. |
| 2021/0121662 | A1* | 4/2021 | Shin .................. A61B 18/1492 |
| 2021/0307823 | A1 | 10/2021 | Urbanski et al. |
| 2021/0338318 | A1 | 11/2021 | Davies et al. |
| 2021/0369336 | A1 | 12/2021 | Davies et al. |
| 2022/0151681 | A1 | 5/2022 | Leung et al. |
| 2022/0240979 | A1 | 8/2022 | Urbanski et al. |
| 2022/0354572 | A1 | 11/2022 | Davies et al. |
| 2023/0404649 | A1 | 12/2023 | Kaneko |

FOREIGN PATENT DOCUMENTS

| | | | |
|---|---|---|---|
| JP | 2016-509942 A | 4/2016 |
| JP | 2019-177150 A | 10/2019 |
| WO | WO2016/203977 A1 | 12/2016 |

* cited by examiner

[Fig. 1]
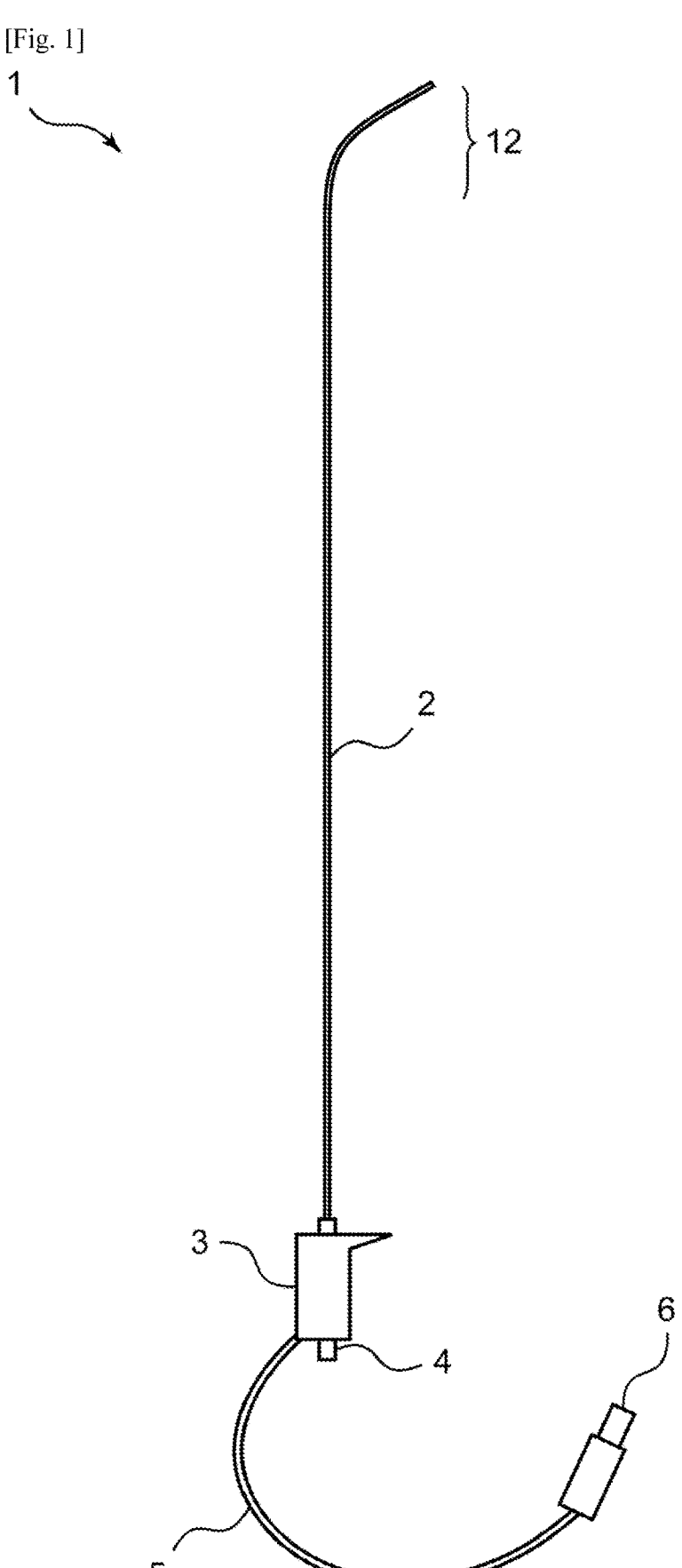

[Fig. 4]
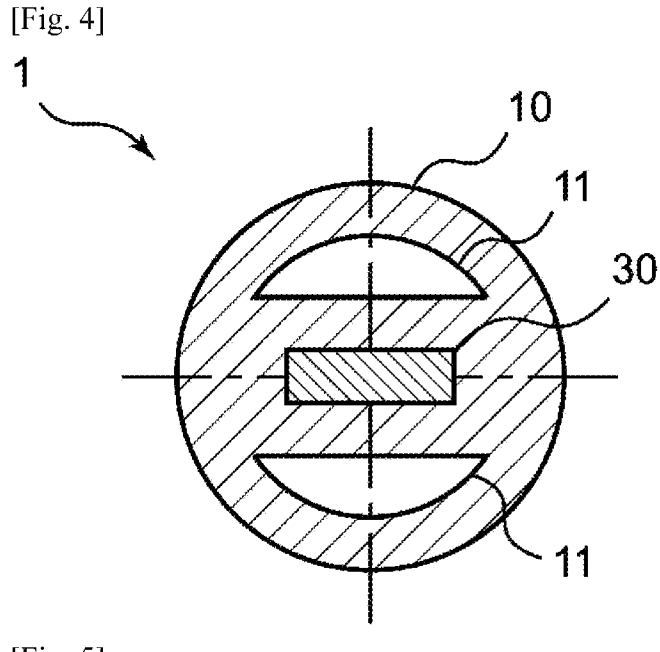
[Fig. 5]
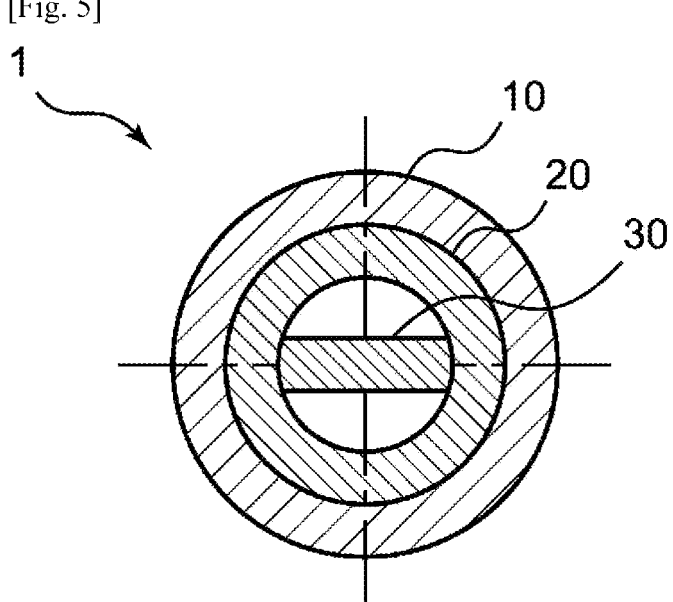

[Fig. 6]
[Fig. 7]
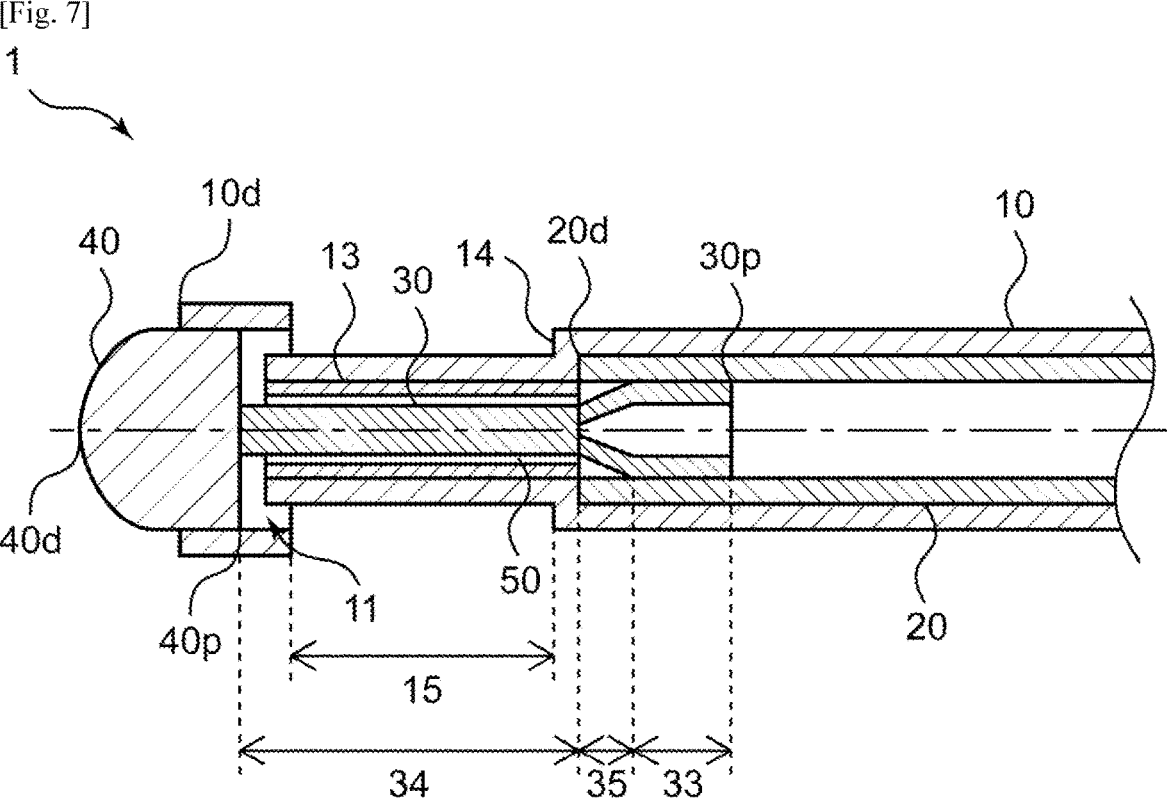

[Fig. 8]
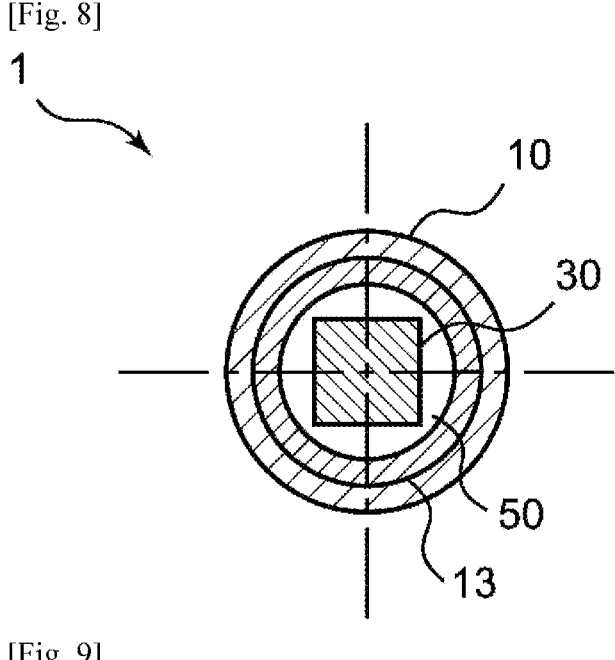
[Fig. 9]
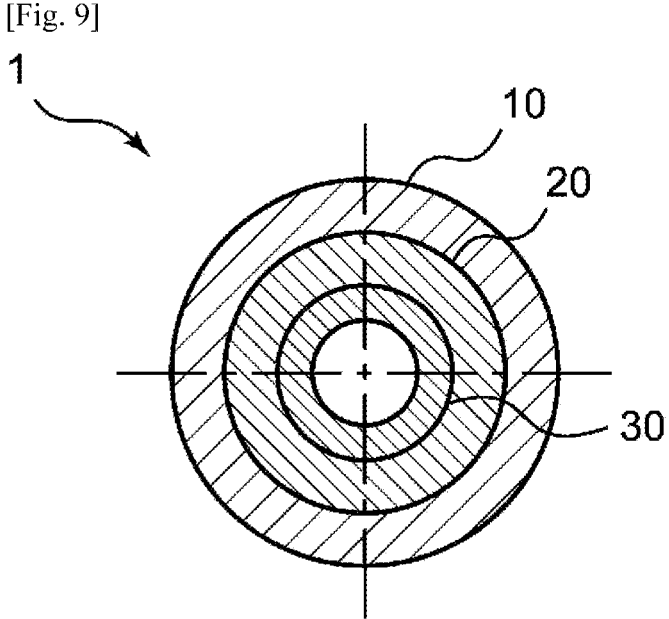

[Fig. 10]
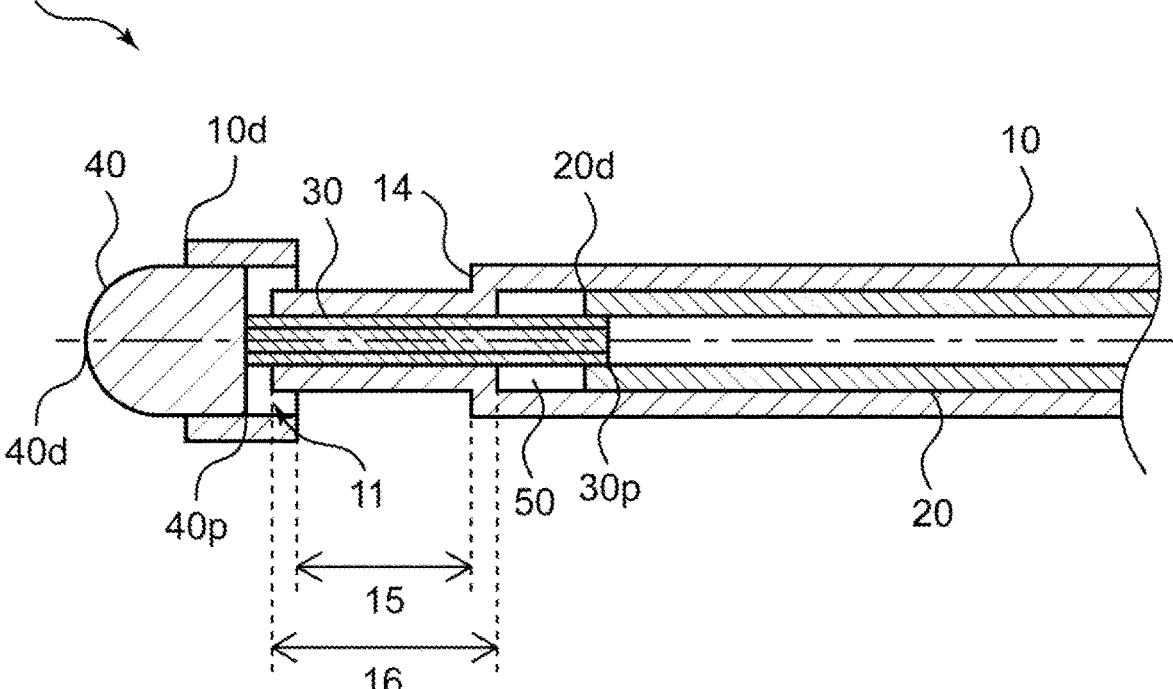
[Fig. 11]

[Fig. 12]
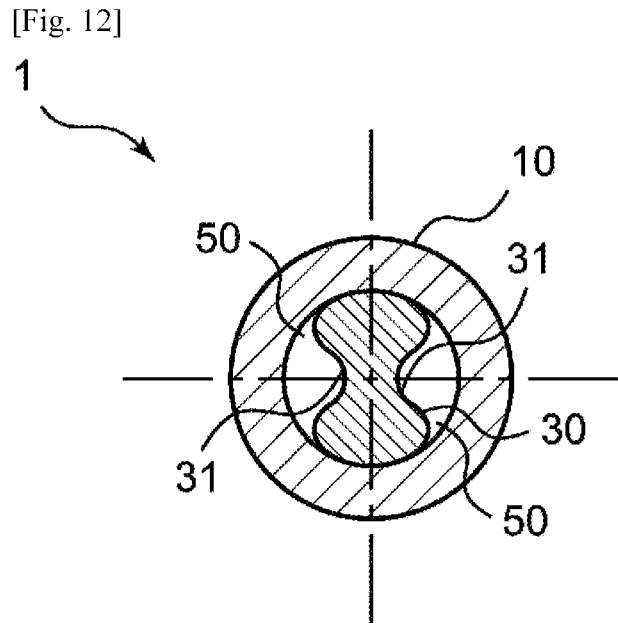
[Fig. 13]
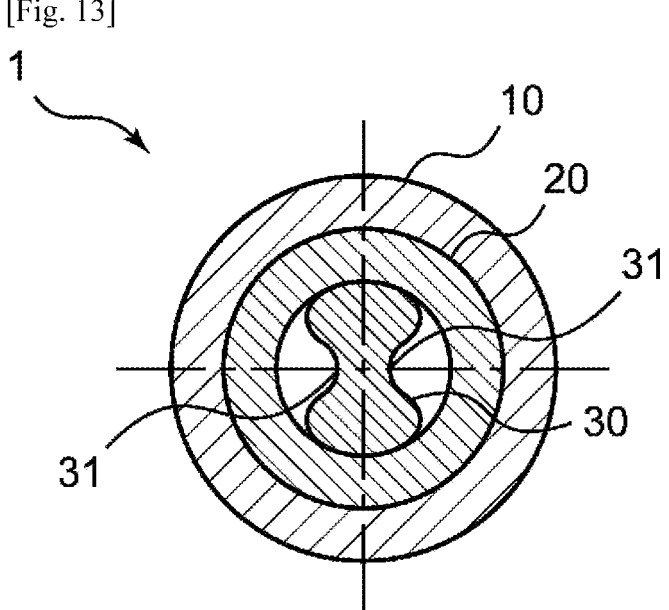

[Fig. 14]
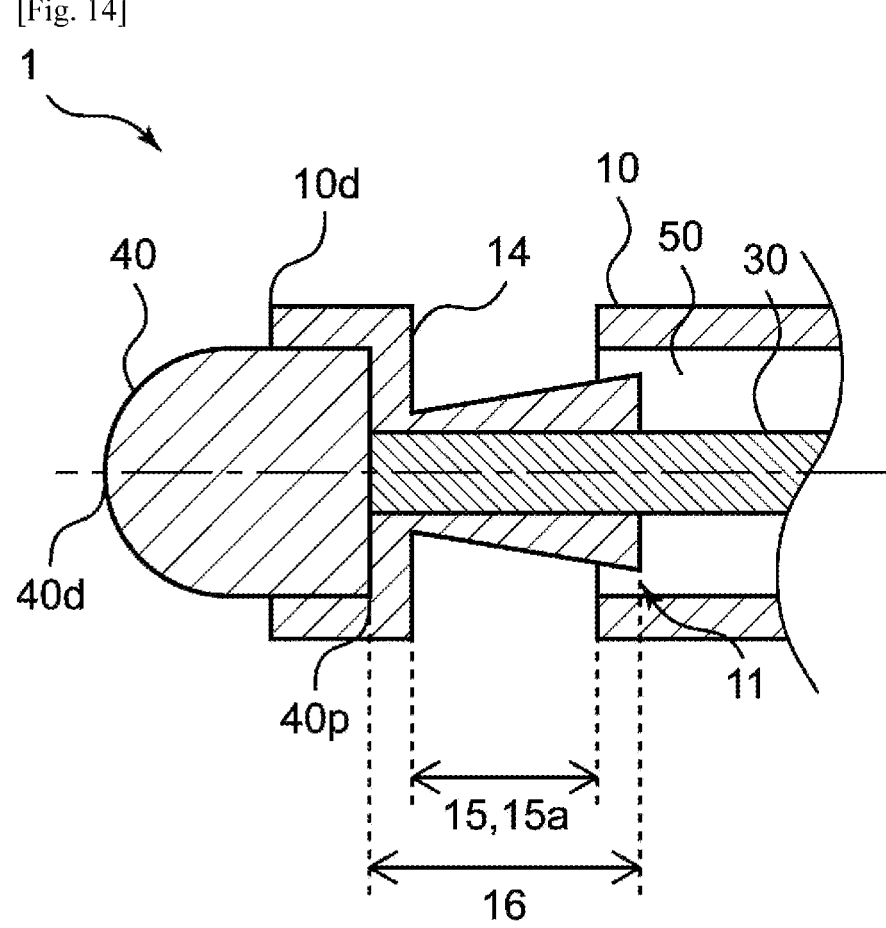

[Fig. 15]
1
40
40d
10d
14
10
50
30
11
40p
15,15b
16
[Fig. 16]
1
40
30 10d
10
40p 41
11
20
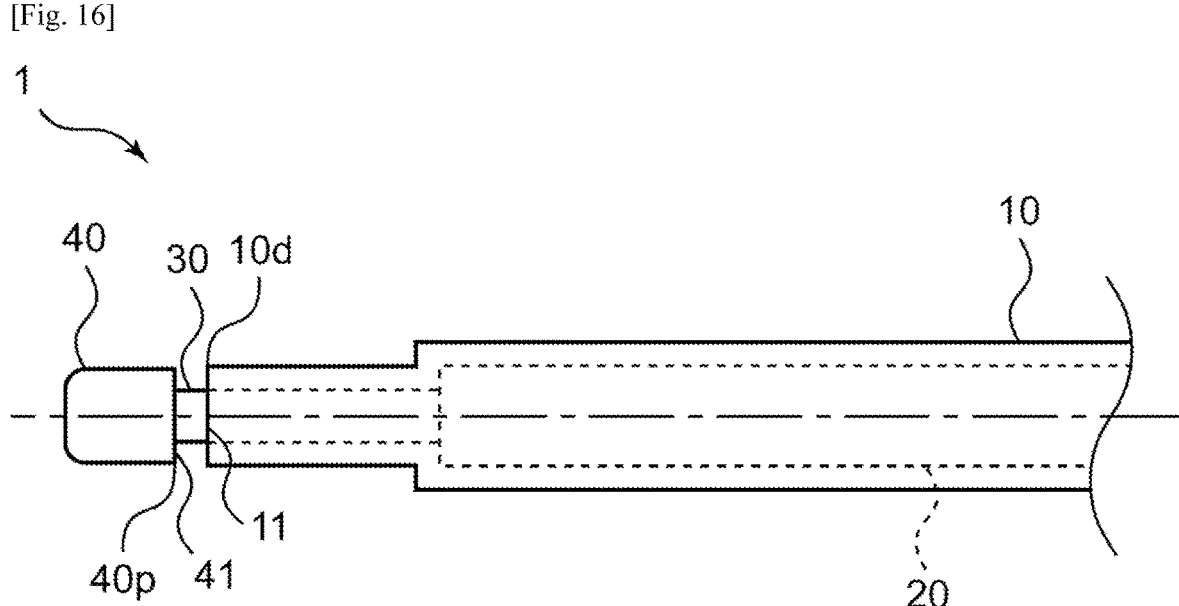

[Fig. 17]
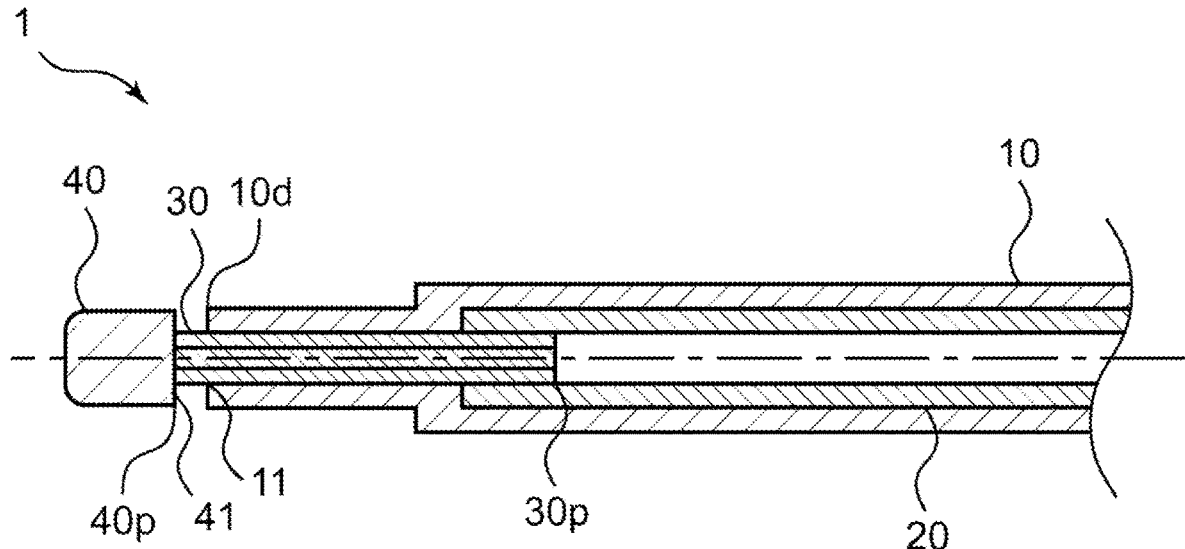
[Fig. 18]
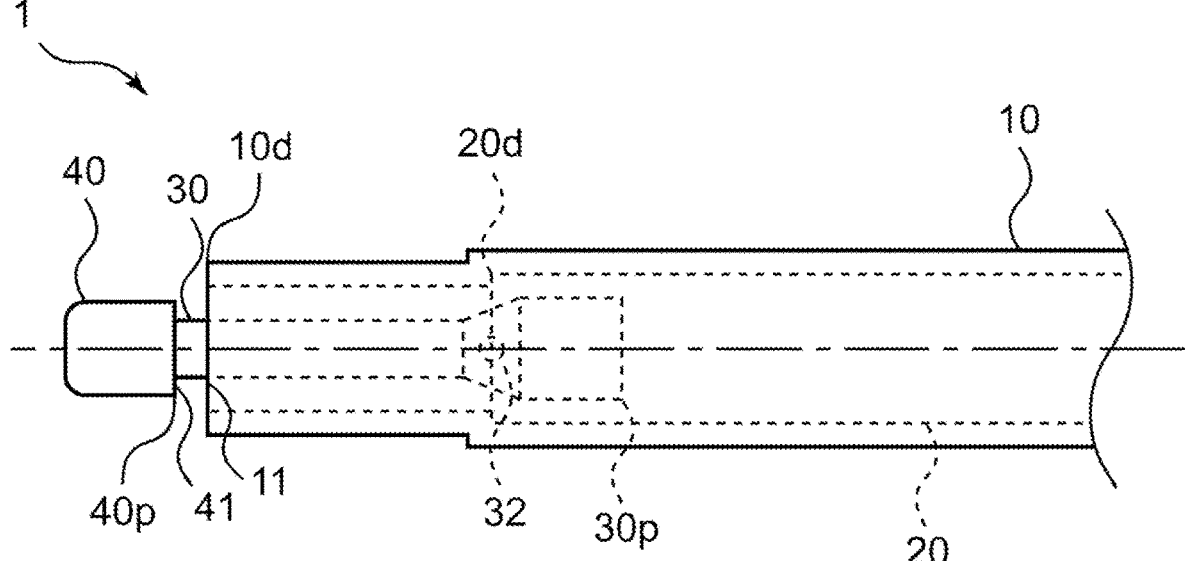

[Fig. 19]
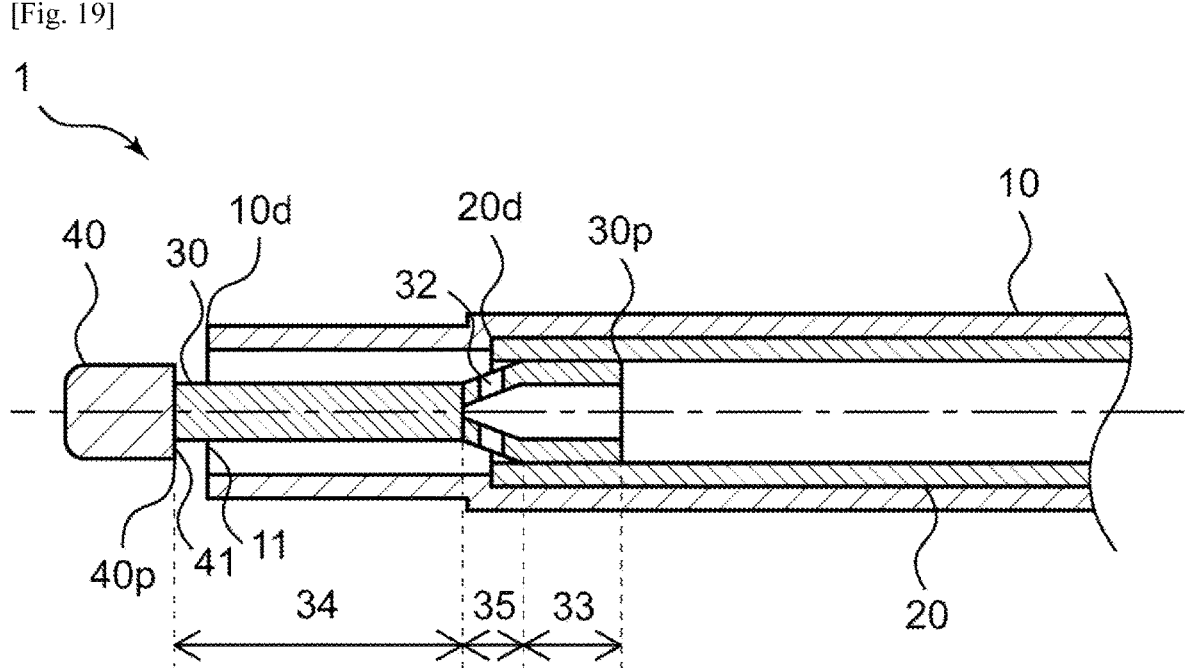

PUNCTURING DEVICE

TECHNICAL FIELD

The present invention relates to a puncturing device that punctures a biological tissue of a portion of the atrial septum or the like.

BACKGROUND ART

A catheter having an electrode is used in a test and a therapy for an arrhythmia such as atrial fibrillation (AF) or atrioventricular reentrant tachycardia (AVRT). At the time of the test, an operator inserts the electrode catheter into a heart chamber and measures an intracardiac potential, to identify an abnormal site, of the heart, that is the cause of the arrhythmia. At the time of the therapy, an operator performs a so-called ablation surgery in which energy including high-frequency current is caused to flow from the electrode of the catheter to a cardiac muscle that is the cause of the arrhythmia so as to necrose the generation source of the arrhythmia, thereby electrically separating the generation source from the heart. In addition, if, at the time of the test or the therapy, atrial fibrillation naturally occurs or atrial fibrillation is caused in order to identify an abnormal site of the heart, the operator gives electrical stimulation to the heart from the electrode of the catheter, to perform defibrillation.

At the time of performing the ablation surgery, the Brockenbrough method as a puncturing method in which a Brockenbrough needle (septum puncturing needle) is used to puncture the fossa ovalis which is a portion of the atrial septum from the right atrium so as to open an insertion path for a catheter is employed in order to deliver the catheter from the right atrium side to the left atrium side.

In the Brockenbrough method, while the positions of the device and the fossa ovalis are being checked through intracardiac echocardiography or X-ray irradiation, the tip of the septum puncturing needle is pressed against the fossa ovalis, and current is conducted to the septum puncturing needle, to cauterize and penetrate the fossa ovalis. Presence/absence of a puncture hole in the fossa ovalis is ascertained as follows. That is, in a state where the fossa ovalis is penetrated by the septum puncturing needle, a liquid such as a physiological saline or a contrast medium is caused to flow from the tip of the septum puncturing needle, and intracardiac echocardiography or X-ray irradiation is performed to check whether the liquid flows to the left atrium side.

As the septum puncturing needle to be used in the Brockenbrough method, for example, Patent Literature 1 describes an electrode catheter. The electrode catheter includes a catheter shaft, an insulative douching member, and a tip electrode. A plurality of douching openings for douching the surface of the tip electrode with a supplied liquid are formed in the insulative douching member at equiangular intervals. A storing space and branch-off flow paths for the liquid are formed inside the insulative douching member. Guiding grooves for the liquid are formed in a distal end portion of the insulative douching member. Guiding grooves for the liquid are formed in a proximal end portion of the tip electrode. Patent Literature 2 describes a medical device. The medical device includes: a thin and long member that is flexible; and a support spine extending from a distal end to a proximal side inside a distal portion of a lumen. The proximal end of the support spine is located inside the distal portion of the lumen. Patent Literature 3 describes a high-frequency treatment instrument. The high-frequency treatment instrument includes a sheath, an electrode member, a distal end member, and a liquid sending means. The electrode member includes: a rod-like electrode portion; and a large-diameter portion made from an insulation material and having an electrode hole. A buffer member is provided between the distal end member and the large-diameter portion. Patent Literature 4 describes an electrosurgical device. The electrosurgical device includes: a thin and long member in which a lumen for a fluid is delimited; and a distal portion having an electrode and a distal face. The distal face has an opening delimited therein and includes a non-cutting portion and a cutting portion configured to transmit energy for puncturing a tissue. A distal surface of the electrode constitutes the cutting portion. A part of the cutting portion is formed as a leading part that partially encloses the periphery of the opening. At least one of the distal portion or the electrode of the electrosurgical device has an outer diameter decreasing toward the distal end of the electrosurgical device.

CITATION LIST

Patent Literature

PATENT LITERATURE 1: JP 2012-135338 A
PATENT LITERATURE 2: JP 2016-509942 T
PATENT LITERATURE 3: WO 2016/203977
PATENT LITERATURE 4: JP 2019-177150 A

SUMMARY OF INVENTION

Technical Problem

After the fossa ovalis is punctured with a puncturing needle, a liquid such as a physiological saline or a contrast medium is caused to flow into the left atrium from an opening in a tip portion of the puncturing needle, and checking as to penetration of the fossa ovalis is performed by using an ultrasonograph or an X-ray fluoroscope. At this time, with a puncturing needle such as one in any of Patent Literatures 1 to 4, a problem arises in that the visibility, of the liquid such as the physiological saline or the contrast medium, in intracardiac echocardiography or X-ray irradiation is poor, and checking as to penetration of the fossa ovalis is difficult to perform.

The present invention has been made in view of the aforementioned circumstances, and an object of the present invention is to provide a puncturing device that can eject a liquid such as a physiological saline or a contrast medium over a wide range inside the left atrium and that enables increase in the visibility in intracardiac echocardiography or X-ray irradiation.

Solution to Problem

A first puncturing device, which solves the above problem, comprises a resin tube having a distal end and a proximal end, and extending in a longitudinal direction; a metal tube disposed in a lumen of the resin tube; a metal member disposed at a distal end portion of the metal tube; and a metal tip disposed at a distal end portion of the metal member, wherein the resin tube includes a flow path which is present between an inner surface of the resin tube and an outer surface of the metal member and which is in communication with a lumen of the metal tube, the distal end of the resin tube is present between a distal end and a proximal end of the metal tip, the resin tube further includes an opening portion through which the flow path and outside of the resin tube are in communication with each other, and the opening portion is present on a distal side relative to a distal end of the metal tube and on a proximal side relative to the proximal end of the metal tip.

A second puncturing device, which solves the above problem, comprises a resin tube having a distal end and a proximal end, and extending in a longitudinal direction; a metal tube disposed in a lumen of the resin tube; a metal member disposed at a distal end portion of the metal tube; and a metal tip disposed at a distal end portion of the metal member, wherein the resin tube includes a flow path which is present between an inner surface of the resin tube and an outer surface of the metal member and which is in communication with a lumen of the metal tube, the resin tube further includes an opening portion through which the flow path and outside of the resin tube are in communication with each other, and the opening portion is present on a distal side relative to a distal end of the metal tube and on a proximal side relative to a proximal end of the metal tip.

In the puncturing device of the present invention, it is preferable that the metal member has an inner cavity opened to at least the proximal side, the metal member includes a large-diameter portion and a small-diameter portion which is located on the distal side relative to the large-diameter portion and which has a smaller outer diameter than the large-diameter portion, and the metal member further includes a hole through which the lumen of the metal tube and a space between the inner surface of the resin tube and the outer surface of the metal member are in communication with each other.

In the puncturing device of the present invention, it is preferable that the opening portion is formed in a surface, of the resin tube, perpendicular to the longitudinal direction.

In the puncturing device of the present invention, it is preferable that the opening portion is an opening oriented to the distal side, and a fluid to be ejected from the opening portion is ejected so as to come into contact with the proximal end of the metal tip.

In the puncturing device of the present invention, it is preferable that the opening portion is an opening oriented to the proximal side.

In the puncturing device of the present invention, it is preferable that the metal member has a recessed portion extending in a longitudinal direction of the metal member.

In the puncturing device of the present invention, it is preferable that a cross-sectional shape of the metal member perpendicular to the longitudinal direction is a polygonal shape.

In the puncturing device of the present invention, it is preferable that a cross-sectional area of the metal member is larger than a cross-sectional area of the flow path in a cross section perpendicular to a longitudinal direction of the metal member.

In the puncturing device of the present invention, it is preferable that the metal member has a portion at which the outer surface of the metal member is at least partially in contact with the inner surface of the resin tube.

In the puncturing device of the present invention, it is preferable that the metal member has, on the distal side relative to the distal end of the metal tube, no portion in contact with the inner surface of the resin tube.

In the puncturing device of the present invention, it is preferable that the resin tube has, on the proximal side relative to the proximal end of the metal tip, an opposed surface opposed to the opening portion.

In the puncturing device of the present invention, it is preferable that the resin tube has, on the proximal side relative to the opposed surface, a narrowed portion having an outer diameter smaller than an outer diameter of the resin tube on the proximal side relative to the opening portion.

In the puncturing device of the present invention, it is preferable that the resin tube has a contact portion in contact with the metal member, and the opening portion is present on the proximal side relative to the contact portion.

In the puncturing device of the present invention, it is preferable that the resin tube has a contact portion in contact with the metal member, and the opening portion is present on the distal side relative to the contact portion.

In the puncturing device of the present invention, it is preferable that the resin tube has, on the proximal side relative to the opposed surface, a narrowed portion having an outer diameter smaller than an outer diameter of the resin tube on the proximal side relative to the opening portion, and the narrowed portion has a diameter-decreasing portion having an outer diameter decreasing from the proximal side toward the distal side.

In the puncturing device of the present invention, it is preferable that the resin tube has, on the proximal side relative to the opposed surface, a narrowed portion having an outer diameter smaller than an outer diameter of the resin tube on the proximal side relative to the opening portion, and the narrowed portion has a diameter-increasing portion having an outer diameter increasing from the proximal side toward the distal side.

In the puncturing device of the present invention, it is preferable that the resin tube has a reinforcing member on the distal side relative to the distal end of the metal tube.

In the puncturing device of the present invention, it is preferable that the reinforcing member is a metal tubular member, and the reinforcing member is disposed on the inner surface of the resin tube.

Advantageous Effects of Invention

In the first puncturing device according to the present invention, the resin tube includes the flow path which is present between the inner surface of the resin tube and the outer surface of the metal member and which is in communication with the lumen of the metal tube, the distal end of the resin tube is present between the distal end and the proximal end of the metal tip, the resin tube further includes an opening portion through which the flow path and the outside of the resin tube are in communication with each other, and the opening portion is present on the distal side relative to the distal end of the metal tube and on the proximal side relative to the proximal end of the metal tip. Consequently, it becomes possible to increase the width of the flow path and the size of the opening portion while maintaining the rigidity of the distal end portion of the puncturing device for the insertability of the puncturing device into a lumen, inside a living body, of a blood vessel or the like and ease of puncturing of the fossa ovalis by the puncturing device. Therefore, a liquid such as a physiological saline or a contrast medium can be ejected over a wide range inside the left atrium, whereby the visibility in intracardiac echocardiography or X-ray irradiation can be increased.

BRIEF DESCRIPTION OF DRAWINGS

FIG. 1 is a plan view of a first puncturing device according to an embodiment of the present invention.

FIG. 2 is a plan view of a distal end portion of the puncturing device shown in FIG. 1.

FIG. 3 is a cross-sectional view taken along a longitudinal direction of the puncturing device shown in FIG. 2.

FIG. 4 is a cross-sectional view, at IV-IV, of the puncturing device shown in FIG. 2.

FIG. 5 is a cross-sectional view, at V-V, of the puncturing device shown in FIG. 2.

FIG. 6 is a plan view of a distal end portion of a first puncturing device according to another embodiment of the present invention.

FIG. 7 is a cross-sectional view taken along the longitudinal direction of the puncturing device shown in FIG. 6.

FIG. 8 is a cross-sectional view, at VIII-VIII, of the puncturing device shown in FIG. 6.

FIG. 9 is a cross-sectional view, at IX-IX, of the puncturing device shown in FIG. 6.

FIG. 10 is a plan view of a distal end portion of a first puncturing device according to still another embodiment of the present invention.

FIG. 11 is a cross-sectional view taken along the longitudinal direction of the puncturing device shown in FIG. 10.

FIG. 12 is a cross-sectional view, at XII-XII, of the puncturing device shown in FIG. 10.

FIG. 13 is a cross-sectional view, at XIII-XIII, of the puncturing device shown in FIG. 10.

FIG. 14 is an enlarged view of a distal end portion of a first puncturing device according to a different embodiment of the present invention.

FIG. 15 is an enlarged view of a distal end portion of a first puncturing device according to a still different embodiment of the present invention.

FIG. 16 is a plan view of a distal end portion of a second puncturing device according to an embodiment of the present invention.

FIG. 17 is a cross-sectional view taken along the longitudinal direction of the puncturing device shown in FIG. 16.

FIG. 18 is a plan view of a distal end portion of a second puncturing device according to another embodiment of the present invention.

FIG. 19 is a cross-sectional view taken along the longitudinal direction of the puncturing device shown in FIG. 18.

DESCRIPTION OF EMBODIMENTS

Hereinafter, the present invention is specifically described below based on the following embodiments; however, the present invention is not restricted by the embodiments described below of course, and can be certainly put into practice after appropriate modifications within in a range meeting the gist of the above and the below, all of which are included in the technical scope of the present invention. In the drawings, hatching or a reference sign for a member may be omitted for convenience, and in such a case, the description and other drawings should be referred to. In addition, sizes of various members in the drawings may differ from the actual sizes thereof, since priority is given to understanding the features of the present invention.

Firstly, a first puncturing device according to the present invention will be described.

Figures 2, 3:
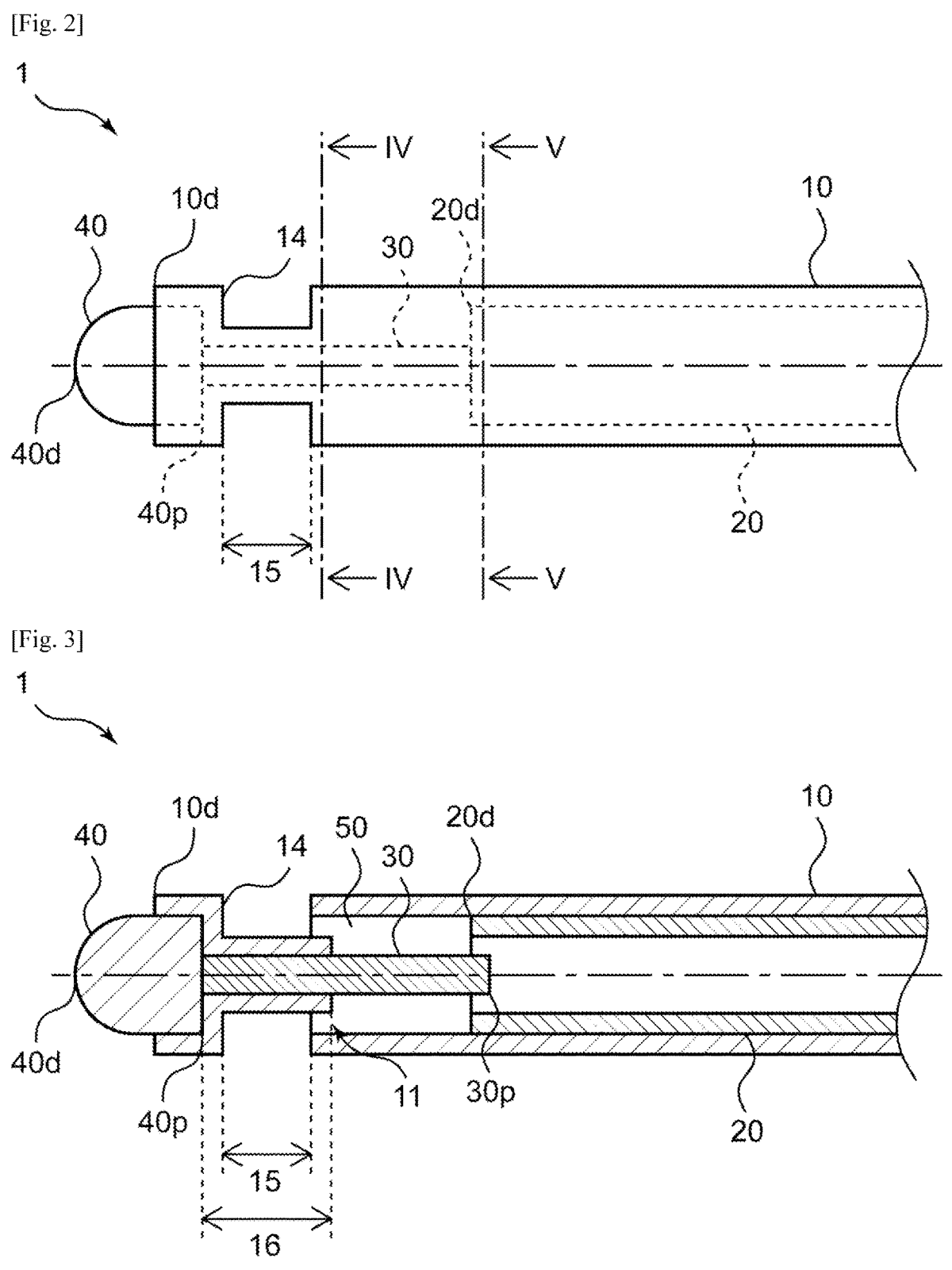

FIG. 1 is a plan view of a first puncturing device 1 according to an embodiment of the present invention, FIG. 2 is a plan view of a distal end portion of the puncturing device 1, FIG. 3 is a cross-sectional view taken along a longitudinal direction of the puncturing device 1, and FIG. 4 and FIG. 5 are cross-sectional views perpendicular to the longitudinal direction of the puncturing device 1. The longitudinal direction of the puncturing device 1 can be rephrased as the distal-proximal direction of the puncturing device 1. The diameter direction of a resin tube 10 in the puncturing device 1 is a direction perpendicular to the longitudinal axis of the resin tube 10 and is the radial direction of the resin tube 10. The circumferential direction of the resin tube 10 in the puncturing device 1 is a direction around the circumference of the resin tube 10.

The first puncturing device 1 according to the present invention includes: a resin tube 10 having a distal end 10d and a proximal end, and extending in the longitudinal direction; a metal tube 20 disposed in a lumen of the resin tube 10; a metal member 30 disposed at a distal end portion of the metal tube 20; and a metal tip 40 disposed at a distal end portion of the metal member 30. The resin tube 10 includes a flow path 50 which is present between an inner surface of the resin tube 10 and an outer surface of the metal member 30 and which is in communication with a lumen of the metal tube 20, the distal end 10d of the resin tube 10 is present between a distal end 40d and a proximal end 40p of the metal tip 40, the resin tube 10 further includes an opening portion 11 through which the flow path 50 and outside of the resin tube 10 are in communication with each other, and the opening portion 11 is present on a distal side relative to a distal end 20d of the metal tube 20 and on a proximal side relative to the proximal end 40p of the metal tip 40.

The puncturing device 1 is used for, for example, puncturing the fossa ovalis which is a portion of the atrial septum so as to open an insertion path for delivering a catheter for use in an ablation surgery or the like from the right atrium to the left atrium.

In the present invention, the proximal side refers to the hand side, of a user, in a direction in which the puncturing device 1 extends, and the distal side refers to the opposite side to the proximal side, i.e., the treatment target side. The direction in which the puncturing device 1 extends is referred to as the longitudinal direction. In FIG. 1, the lower side of the drawing is the proximal side, and the upper side of the drawing is the distal side. In each of FIG. 2 and FIG. 3, the right side of the drawing is the proximal side, and the left side of the drawing is the distal side.

As shown in FIG. 1 and FIG. 2, the puncturing device 1 may have a shaft 2 including the resin tube 10, the metal tube 20, the metal member 30, and the metal tip 40 and may have a handle 3 at a proximal end portion of the shaft 2. The handle 3 preferably has a syringe port 4 from which a liquid such as a physiological saline or a contrast medium is sent into the flow path 50 through the shaft 2. If the handle 3 has the syringe port 4, connection of a syringe or the like to the syringe port 4 enables the liquid to be sent into the flow path 50. This makes it easy to perform an operation of injecting the liquid into the body from the tip of the puncturing device 1 in order to check presence/absence of a puncture hole in the fossa ovalis.

The handle 3 preferably has a connector 6 for conducting current to the shaft 2, the connector 6 being connected to the handle 3 via a cable 5. If the handle 3 has the cable 5 and the connector 6, connection of the connector 6 to a power supply for conduction of high-frequency current enables the metal tube 20, the metal member 30, and the metal tip 40 of the shaft 2 to be electrically connected to each other. Therefore, it becomes possible to conduct current from the metal tip 40 to a counter electrode plate, whereby puncturing of the fossa ovalis is facilitated.

The shaft 2 preferably has, at a distal end portion thereof, a bent portion 12 at which the shaft 2 is bent. If the shaft 2 has the bent portion 12 at the distal end portion, it becomes easy to insert the puncturing device 1 into the heart. The angle at which the shaft 2 is bent at the bent portion 12 can be adjusted according to the shape and the state of each of a lumen inside the body and the heart. The bent portion 12 may be located on the proximal side relative to a proximal end 30p of the metal member 30. Alternatively, the bent portion 12 may be provided at a portion in which the metal member 30 is disposed. If the bent portion 12 is provided at the distal end portion of the shaft 2, the operability of the puncturing device 1 can be improved.

The number of lumens of the resin tube 10 not having yet been assembled into the puncturing device 1 may be two or more, but is preferably one. If the number of the lumens of the resin tube 10 is one, it is possible to increase the cross-sectional area, of the lumen, in a direction perpendicular to the longitudinal direction while decreasing the outer diameter of the resin tube 10. Therefore, it becomes easy to dispose the metal tube 20 in the lumen of the resin tube 10, whereby manufacturing of the puncturing device 1 is facilitated.

As shown in FIG. 2 and FIG. 3, the resin tube 10 has the distal end and the proximal end, and extends in the longitudinal direction. A material from which the resin tube 10 is made is preferably an insulative material, and examples of the insulative material include synthetic resins such as: polyolefin-based resins such as polyethylene and polypropylene; polyamide-based resins such as nylons; polyester-based resins such as PET; aromatic polyether ketone-based resins such as PEEK; polyether polyamide-based resins; polyurethane-based resins; polyimide-based resins; fluorine-based resins such as PTFE, PFA, and ETFE; and polyvinyl chloride-based resins. The resin tube 10 may be made from one type of synthetic resin or may contain a plurality of types of synthetic resins. If the material from which the resin tube 10 is made is an insulative material, the metal tube 20 and the metal member 30 can be insulated by the resin tube 10 at the time of current conduction to the metal tip 40. Among these materials, the material from which the resin tube 10 is made preferably contains a fluorine-based resin and more preferably contains PTFE. If the material from which the resin tube 10 is made contains a fluorine-based resin, the slipperiness of the outer surface of the resin tube 10 is increased, whereby the puncturing device 1 can be configured to have favorable insertability.

As the length in the longitudinal direction of the resin tube 10, a length that is appropriate for therapy can be selected, and the length can be set to be, for example, not smaller than 500 mm and not larger than 1200 mm.

The outer diameter of the resin tube 10 is preferably not smaller than 0.3 mm, more preferably not smaller than 0.5 mm, and further preferably not smaller than 0.6 mm. If the lower limit value of the outer diameter of the resin tube 10 is set such that the outer diameter falls within the above range, the rigidity of the resin tube 10 can be increased, whereby the puncturing device 1 can be configured to have favorable insertability into a blood vessel. Meanwhile, the outer diameter of the resin tube 10 is preferably not larger than 2 mm, more preferably not larger than 1.8 mm, and further preferably not larger than 1.5 mm. If the upper limit value of the outer diameter of the resin tube 10 is set such that the outer diameter falls within the above range, the outer diameter of the puncturing device 1 can be made small. Therefore, the minimal invasiveness of the puncturing device 1 can be improved.

The thickness of the resin tube 10 is preferably not smaller than 30 μm, more preferably not smaller than 50 μm, and further preferably not smaller than 100 μm. If the lower limit value of the thickness of the resin tube 10 is set such that the thickness falls within the above range, insulation can be performed by the resin tube 10 at the time of current conduction to the metal tip 40. Therefore, an unintended site inside the body can be prevented from being cauterized. Meanwhile, the thickness of the resin tube 10 is preferably not larger than 350 μm, more preferably not larger than 300 μm, and further preferably not larger than 250 μm. If the upper limit value of the thickness of the resin tube 10 is set such that the thickness falls within the above range, the outer diameter of the resin tube 10 is prevented from excessively increasing, whereby the puncturing device 1 becomes a minimally invasive puncturing device.

As shown in FIG. 2 to FIG. 5, the metal tube 20 is disposed in the lumen of the resin tube 10. That is, the resin tube 10 is disposed outward of the metal tube 20. The number of the lumens of the metal tube 20 may be two or more, but is preferably one. If the metal tube 20 has one lumen, the cross-sectional area, of the lumen, in a direction perpendicular to the longitudinal direction can be increased, whereby the flow amount of a liquid to be sent into the flow path 50 can be increased.

Examples of a material from which the metal tube 20 is made include metals such as stainless steel, carbon steel, and nickel-titanium alloys. The material from which the metal tube 20 is made is preferably stainless steel. If the material from which the metal tube 20 is made is stainless steel, the rigidity of the metal tube 20 is increased. As a result, the pushability of the puncturing device 1 can be improved, and puncturing of the fossa ovalis by the puncturing device 1 can be facilitated.

As the length in the longitudinal direction of the metal tube 20, a length that is appropriate for therapy can be selected, and the length can be set to be, for example, not smaller than 500 mm and not larger than 1200 mm.

The outer diameter of the metal tube 20 is preferably not smaller than 0.5 mm, more preferably not smaller than 0.7 mm, and further preferably not smaller than 1 mm. If the lower limit value of the outer diameter of the metal tube 20 is set such that the outer diameter falls within the above range, the rigidity of the metal tube 20 is increased. Thus, the pushability of the puncturing device 1 can be improved, and puncturing of the fossa ovalis by the puncturing device 1 can be facilitated. Meanwhile, the outer diameter of the metal tube 20 is preferably not larger than 2 mm, more preferably not larger than 1.8 mm, and further preferably not larger than 1.5 mm. If the upper limit value of the outer diameter of the metal tube 20 is set such that the outer diameter falls within the above range, it is easy to sufficiently ensure the cross-sectional area of the lumen in a cross section of the metal tube 20 perpendicular to the longitudinal direction, and the amount of a liquid to be sent into the flow path 50 can be made sufficient.

The thickness of the metal tube 20 is preferably not smaller than 100 μm, more preferably not smaller than 150 μm, and further preferably not smaller than 200 μm. If the lower limit value of the thickness of the metal tube 20 is set such that the thickness falls within the above range, the rigidity of the metal tube 20 is increased. Therefore, the pushability of the puncturing device 1 can be improved, and puncturing of the fossa ovalis by the puncturing device 1 can be facilitated. Meanwhile, the thickness of the metal tube 20 is preferably not larger than 350 μm, more preferably not larger than 300 μm, and further preferably not larger than 250 μm. If the upper limit value of the thickness of the metal tube 20 is set such that the thickness falls within the above range, the outer diameter of the metal tube 20 is prevented from excessively increasing. As a result, the diameter of the puncturing device 1 can be decreased.

As shown in FIG. 3, the metal member 30 is joined to the distal end portion of the metal tube 20. Examples of a method for joining the metal member 30 to the distal end portion of the metal tube 20 include ones involving: connection through welding, brazing with a solder or the like, bonding, crimping, or the like; press-fitting of the metal member 30 into the metal tube 20; fitting of the metal tube 20 and the metal member 30 with each other; and connection between the metal tube 20 and the metal member 30 via another component. Among these methods, the method for joining the metal member 30 to the distal end portion of the metal tube 20 is preferably one involving fixation through welding, brazing, bonding, or the like, and is more preferably one involving welding. By fixing the distal end portion of the metal tube 20 and the metal member 30 to each other, the joining strength between the metal tube 20 and the metal member 30 is increased. Therefore, even when the puncturing device 1 is curved, the metal member 30 is less likely to be detached from the metal tube 20.

Examples of a material from which the metal member 30 is made include metals such as stainless steel, carbon steel, and nickel-titanium alloys. The material from which the metal member 30 is made is preferably stainless steel. If the material from which the metal member 30 is made is stainless steel, the rigidity of the metal member 30 can be increased. Therefore, the rigidity of the distal end portion of the puncturing device 1 is also increased, and puncturing of the fossa ovalis by the puncturing device 1 is facilitated.

The diameter of a circumscribed circle around the cross-sectional shape, of the proximal end 30*p* of the metal member 30, perpendicular to the longitudinal direction of the metal member 30 is preferably smaller than the inner diameter of the metal tube 20 at the distal end 20*d* of the metal tube 20. If the diameter of the circumscribed circle around the cross-sectional shape of the proximal end 30*p* of the metal member 30 is smaller than the inner diameter of the distal end 20*d* of the metal tube 20, a proximal end portion of the metal member 30 can be inserted into the distal end portion of the metal tube 20, and the joining strength between the metal tube 20 and the metal member 30 can be increased.

As shown in FIG. 2 and FIG. 3, the metal tip 40 is disposed at the distal end portion of the metal member 30. Regarding the metal tip 40, another member composing the metal tip 40 may be directly joined to the distal end portion of the metal member 30, or the metal tip 40 may be indirectly joined to the distal end portion of the metal member 30 via, for example, an intermediate member that is another component different from the metal member 30 and the metal tip 40. The metal tip 40 is disposed at the distal end portion of the metal member 30, and the metal tip 40 and the metal member 30 only have to be integrated with each other and may be in a state of having a seam therebetween or in a state of having no seam therebetween. The metal tip 40 can be joined to the metal member 30 in order to dispose the metal tip 40 at the distal end portion of the metal member 30.

Examples of a specific method for joining the metal tip 40 to the distal end portion of the metal member 30 include ones involving: connection through welding, brazing with a solder or the like, bonding, crimping, or the like; press-fitting of the metal member 30 into the metal tip 40; fitting of the metal member 30 and the metal tip 40 with each other; and connection between the metal member 30 and the metal tip 40 via another component. Among these methods, the method for joining the metal tip 40 to the distal end portion of the metal member 30 is preferably one involving fixation through welding, brazing, bonding, or the like, and is more preferably one involving welding. By fixing the distal end portion of the metal member 30 and the metal tip 40 to each other, the metal tip 40 can be firmly joined to the metal member 30. Therefore, when the metal tip 40 is pressed against the fossa ovalis in order to, for example, puncture the fossa ovalis, the metal tip 40 is less likely to fall off from the metal member 30, whereby the puncturing device 1 can be configured to have a high durability.

Examples of a material from which the metal tip 40 is made include metals such as stainless steel, carbon steel, and nickel-titanium alloys. The material from which the metal tip 40 is made is preferably the same as the material from which the metal member 30 is made. If the material from which the metal tip 40 is made is the same as the material from which the metal member 30 is made, the metal member 30 and the metal tip 40 are easily joined together, and the joining strength between the metal member 30 and the metal tip 40 can be increased.

As shown in FIG. 2 and FIG. 3, a distal end portion of the metal tip 40 preferably has the shape of a curved surface. If the distal end portion of the metal tip 40 has the shape of a curved surface, the metal tip 40 can be made less likely to injure a lumen, inside the body, of a blood vessel or the like when the metal tip 40 comes into contact with the lumen inside the body. As a result, the metal tip 40 becomes less likely to injure or puncture an unintended site.

As described above, since the metal tube 20 and the metal member 30 of the shaft 2 are joined together, and the metal member 30 and the metal tip 40 of the shaft 2 are joined together, three members which are the metal tube 20, the metal member 30, and the metal tip 40 are electrically connected to each other, whereby current conduction can be performed.

As shown in FIG. 3 and FIG. 4, the resin tube 10 includes the flow path 50 which is present between the inner surface of the resin tube 10 and the outer surface of the metal member 30 and which is in communication with the lumen of the metal tube 20. As shown in FIG. 2 and FIG. 3, the distal end 10*d* of the resin tube 10 is present between the distal end 40*d* and the proximal end 40*p* of the metal tip 40.

As shown in FIG. 3, the resin tube 10 further includes the opening portion 11 through which the flow path 50 and the outside of the resin tube 10 are in communication with each other. The opening portion 11 is present on the distal side relative to the distal end 20*d* of the metal tube 20 and on the proximal side relative to the proximal end 40*p* of the metal tip 40.

Since the distal end 10*d* of the resin tube 10 is present between the distal end 40*d* and the proximal end 40*p* of the metal tip 40, and the opening portion 11 is present on the distal side relative to the distal end 20*d* of the metal tube 20 and on the proximal side relative to the proximal end 40*p* of the metal tip 40, it is possible to increase the width of the flow path 50 while maintaining the rigidity of the distal end portion of the puncturing device 1 by the metal member 30. Therefore, the pushability of the puncturing device 1 and ease of puncturing of the fossa ovalis by the puncturing device 1 are improved, and furthermore, a large amount of liquid such as a physiological saline or a contrast medium can be ejected, whereby the visibility in intracardiac echocardiography or X-ray irradiation can be increased.

As shown in FIG. 4, the number of the flow paths 50 is preferably two or more. If the number of the flow paths 50 provided in the resin tube 10 is two or more, it becomes easy to eject a liquid over a wide range in the diameter direction of the resin tube 10 when the liquid is ejected from the opening portion 11 to the outside. As a result, it becomes easy to check presence/absence of a puncture hole in the fossa ovalis by means of intracardiac echocardiography or X-ray irradiation.

The resin tube 10 may be one tube from the distal end to the proximal end thereof or may be composed of a plurality of tubes. In the case where the resin tube 10 is composed of a plurality of tubes in the longitudinal direction, the tubes need to be joined together so as to form one tube. In this case, the boundaries between the joined portions do not have to be definite. Although not shown, in the case where the resin tube 10 is composed of a plurality of tubes, the resin tube 10 may have a distal-side resin tube and a proximal-side resin tube, the metal member 30 may be disposed in a lumen of the distal-side resin tube, and the metal tube 20 may be disposed in a lumen of the proximal-side resin tube. Still another tube that covers the joined portion between the metal tube 20 and the metal member 30 may be disposed. If the resin tube 10 has the distal-side resin tube and the proximal-side resin tube, the distal-side resin tube can be made so as to have a size and a material that are suitable for the metal member 30, and the proximal-side resin tube can be made so as to have a size and a material that are suitable for the metal tube 20. As a result, it becomes easy to perform a step of disposing the metal tube 20 and the metal member 30 into the lumens of the resin tube 10.

In the case where the resin tube 10 has the distal-side resin tube and the proximal-side resin tube, although not shown, a proximal end of the distal-side resin tube is preferably present on the proximal side relative to a distal end of the proximal-side resin tube. If the proximal end of the distal-side resin tube is present on the proximal side relative to the distal end of the proximal-side resin tube, the proximal end portion of the distal-side resin tube and the distal end portion of the proximal-side resin tube are superposed on each other. Therefore, it can be made less likely for a liquid such as blood to enter the lumens of the resin tube 10 from the gap between the distal-side resin tube and the proximal-side resin tube when the puncturing device 1 is inserted into a lumen inside the body.

The length of the portion at which the proximal end portion of the distal-side resin tube and the distal end portion of the proximal-side resin tube are superposed on each other can be selected in consideration of influence on the magnitude of the outer diameter of the resin tube 10 and the joining strength. Examples of a method for joining together the proximal end portion of the distal-side resin tube and the distal end portion of the proximal-side resin tube include ones involving heating, bonding, and drawing the proximal end portion of the distal-side resin tube and the distal end portion of the proximal-side resin tube.

Also, the proximal end of the distal-side resin tube is preferably located in the lumen of the proximal-side resin tube. If the proximal end of the distal-side resin tube is located in the lumen of the proximal-side resin tube, the distal end portion of the proximal-side resin tube can be brought into close contact with the outer surface of the distal-side resin tube. Thus, when a liquid is sent into the lumen of the metal tube 20 and the liquid is passing through the flow path 50, the liquid in the flow path 50 can be prevented from leaking to the outside from between the distal-side resin tube and the proximal-side resin tube.

The proximal end of the distal-side resin tube is preferably joined to the distal end of the proximal-side resin tube without any gap therebetween. If the proximal end of the distal-side resin tube is joined to the proximal-side resin tube without any gap therebetween, current transmitted through the metal tube 20, the metal member 30, the metal tip 40, and the like can be made less likely to leak to the outside from the gap between the distal-side resin tube and the proximal-side resin tube when current is conducted to the metal tip 40 via the metal tube 20.

It is preferable that, as shown in FIG. 2 and FIG. 3, the outer diameter of the resin tube 10 at a portion thereof in which the distal end 20*d* of the metal tube 20 is located is larger than the outer diameter of the resin tube 10 at a portion thereof in which the distal end of the metal member 30 is located. If the outer diameter of the resin tube 10 at the portion thereof in which the distal end 20*d* of the metal tube 20 is located is larger than the outer diameter of the resin tube 10 at the portion thereof in which the distal end of the metal member 30 is located, a small-diameter portion 34 on the distal side and a large-diameter portion 33 on the proximal side relative to the small-diameter portion 34 can be formed in the distal end portion of the puncturing device 1. Therefore, for example, in the case of using a dilator in order to insert the puncturing device 1 into a lumen inside the body, employment of a configuration in which only the small-diameter portion 34 is exposed from the dilator makes it possible to easily control the length over which the puncturing device 1 is exposed from the dilator.

FIG. 6 is a plan view of a distal end portion of a puncturing device 1 according to another embodiment of the present invention, FIG. 7 is a cross-sectional view taken along the longitudinal direction of this puncturing device 1, and FIG. 8 and FIG. 9 are cross-sectional views perpendicular to the longitudinal direction of this puncturing device 1. In each of FIG. 6 and FIG. 7, the right side of the drawing is the proximal side, and the left side of the drawing is the distal side.

It is preferable that, as shown in FIG. 6 and FIG. 7: the metal member 30 has a inner cavity opened to at least the proximal side; the metal member 30 includes the large-diameter portion 33 and the small-diameter portion 34 which is located on the distal side relative to the large-diameter portion 33 and which has a smaller outer diameter than the large-diameter portion 33; and the metal member 30 further includes a hole 32 through which the lumen of the metal tube 20 and a space between the inner surface of the resin tube 10 and the outer surface of the metal member 30 are in communication with each other. The hole 32 may be provided in the small-diameter portion 34. The number of the holes 32 provided may be one or may be two or more. In the case where the number of the holes 32 is two or more, the plurality of holes 32 can be provided in the longitudinal direction or the circumferential direction of the metal member 30. The plurality of holes 32 may be provided in the circumferential direction of the metal member 30 in order to eject a liquid from the entire circumference of the resin tube 10 through the opening portion 11 in the distal end 10*d* of the resin tube 10.

If the metal member 30 includes the large-diameter portion 33, the rigidity of the proximal-side portion, of the metal member 30, at which the large-diameter portion 33 is present increases, whereby the pushability of the puncturing device 1 and ease of puncturing of the fossa ovalis by the puncturing device 1 can be improved. If the metal member 30 includes the small-diameter portion 34, the space between the inner surface of the resin tube 10 and the outer surface of the distal-side portion, of the metal member 30, at which the small-diameter portion 34 is present is enlarged, whereby the flow path 50 can be widened. Therefore, the flow amount of a liquid to be ejected from the puncturing device 1 can be increased, whereby the visibility in intracardiac echocardiography or X-ray irradiation can be improved.

As shown in FIG. 7, the inner cavity of the metal member 30 is opened to at least the proximal side. The proximal end of the inner cavity of the metal member 30 is in communication with the lumen of the metal tube 20. The distal end of the inner cavity of the metal member 30 may be coincident with the distal end of the metal member 30 or may be present on an inner side relative to the distal end of the metal member 30, i.e., on the proximal side relative to the distal end of the metal member 30. In consideration of flow of a liquid inside the puncturing device 1, the distal end of the inner cavity of the metal member 30 is preferably coincident with the proximal end of the small-diameter portion 34 of the metal member 30 as shown in FIG. 7.

In the puncturing device 1 in which the metal member 30 includes the large-diameter portion 33, the small-diameter portion 34, and the hole 32, a liquid inside the flow path 50 passes through the lumen of the metal tube 20, the inner cavity of the metal member 30, the hole 32, and the space between the inner surface of the resin tube 10 and the outer surface of the metal member 30, to be ejected to the outside of the resin tube 10. Since the inner diameter of the hole 32 is smaller than the inner diameter of the metal member 30, the flow rate of the liquid increases when the liquid passes through the hole 32. As a result, the liquid can be vigorously ejected to the outside of the resin tube 10 over a wide range, whereby the visibility in intracardiac echocardiography or X-ray irradiation can be increased.

The outer diameter of the large-diameter portion 33 is preferably not lower than 1.1 times, more preferably not lower than 1.3 times, and further preferably not lower than 1.5 times the outer diameter of the small-diameter portion 34. If the lower limit value of the ratio of the outer diameter of the large-diameter portion 33 to the outer diameter of the small-diameter portion 34 is set such that the ratio falls within the above range, the rigidity of the proximal-side portion, of the metal member 30, at which the large-diameter portion 33 is present is sufficiently increased, and the space between the inner surface of the resin tube 10 and the outer surface of the distal-side portion, of the metal member 30, at which the small-diameter portion 34 is present can be sufficiently ensured. Meanwhile, the outer diameter of the large-diameter portion 33 is preferably not higher than 2 times, more preferably not higher than 1.8 times, and further preferably not higher than 1.6 times the outer diameter of the small-diameter portion 34. If the upper limit value of the ratio of the outer diameter of the large-diameter portion 33 to the outer diameter of the small-diameter portion 34 is set such that the ratio falls within the above range, the outer diameter of the distal end portion of the puncturing device 1 is prevented from excessively increasing, whereby minimal invasiveness can be increased.

Next, a second puncturing device according to the present invention will be described. In descriptions about the second puncturing device, the same descriptions as the above descriptions will be omitted.

FIG. 16 is a plan view of a distal end portion of a second puncturing device 1 according to an embodiment of the present invention, and FIG. 17 is a cross-sectional view taken along the longitudinal direction of the puncturing device 1. Also, FIG. 18 is a plan view of a distal end portion of a second puncturing device 1 according to another embodiment of the present invention, and FIG. 19 is a cross-sectional view taken along the longitudinal direction of the puncturing device 1.

Each second puncturing device 1 according to the present invention includes: the resin tube 10 having the distal end 10*d* and the proximal end, and extending in the longitudinal direction; the metal tube 20 disposed in the lumen of the resin tube 10; the metal member 30 disposed at the distal end portion of the metal tube 20; and the metal tip 40 disposed at the distal end portion of the metal member 30. The resin tube 10 includes the flow path 50 which is present between the inner surface of the resin tube 10 and the outer surface of the metal member 30 and which is in communication with the lumen of the metal tube 20, the resin tube 10 further includes the opening portion 11 through which the flow path 50 and the outside of the resin tube 10 are in communication with each other, and the opening portion 11 is present on the distal side relative to the distal end 20*d* of the metal tube 20 and on the proximal side relative to the proximal end 40*p* of the metal tip 40.

The distal end 10*d* of the resin tube 10 may be present between the distal end 40*d* and the proximal end 40*p* of the metal tip 40 as shown in FIG. 2 and FIG. 3 or may be present on the proximal side relative to the proximal end 40*p* of the metal tip 40 as shown in FIG. 16 to FIG. 19. In the case where the distal end 10*d* of the resin tube 10 is present on the proximal side relative to the proximal end 40*p* of the metal tip 40 as shown in FIG. 16 and FIG. 17, the distal end of the flow path 50 is preferably coincident with the distal end 10*d* of the resin tube 10. If the distal end 10*d* of the resin tube 10 is present on the proximal side relative to the proximal end 40*p* of the metal tip 40, the distal end 10*d* of the resin tube 10 is apart from the proximal end 40*p* of the metal tip 40, and a liquid such as a physiological saline or a contrast medium inside the flow path 50 is ejected from the distal end 10*d* of the resin tube 10 to the outside of the resin tube 10. That is, the opening portion 11 is present in the distal end 10*d* of the resin tube 10, and the liquid inside the flow path 50 is ejected from the opening portion 11 to the outside of the resin tube 10. Therefore, the liquid that had been inside the flow path 50 and that has been ejected from the distal end 10*d* of the resin tube 10 can be diffused in the diameter direction of the resin tube 10 and can be ejected over a wide range inside the left atrium, whereby the visibility in intracardiac echocardiography or X-ray irradiation can be increased. The liquid flows along the longitudinal direction of the resin tube 10 through the flow path 50, and thus, is ejected from the distal end 10*d* of the resin tube 10 and flows toward an opposed surface 41 which is a surface at the proximal end of the metal tip 40. The direction of flow of the liquid is changed to the diameter direction of the resin tube 10 by the opposed surface 41.

In the case where the metal member 30 includes the hole 32, the distal end 10*d* of the resin tube 10 is preferably present on the distal side relative to the hole 32 as shown in FIG. 18 and FIG. 19. If the distal end 10*d* of the resin tube 10 is present on the distal side relative to the hole 32, a liquid having passed through the lumens of the metal tube 20 and the metal member 30 and having been ejected from the hole 32 moves to the lumen of the resin tube 10 and is ejected from the distal end 10*d* of the resin tube 10. As a result, the liquid which had been inside the flow path 50 can be diffused over a wide range in the diameter direction of the resin tube 10, whereby the visibility in intracardiac echocardiography or X-ray irradiation can be improved.

It is preferable that, as shown in FIG. 7, a transitional part 35 having a diameter decreasing toward the distal side is provided on the distal side relative to the large-diameter portion 33 and on the proximal side relative to the small-diameter portion 34, and the hole 32 is located in the transitional part 35. If the hole 32 is located in the transitional part 35, a liquid in the inner cavity of the large-diameter portion 33 of the metal member 30 can be efficiently sent via the hole 32 to the space between the inner surface of the resin tube 10 and the outer surface of the portion, of the metal member 30, at which the small-diameter portion 34 is present. In a case where the space between the outer surface of the small-diameter portion 34 and the inner surface of the resin tube 10 is made wider than the space between the outer surface of the large-diameter portion 33 and the inner surface of the resin tube 10, flow of the liquid inside the flow path 50 becomes smooth, whereby it becomes easy to eject a large amount of the liquid from the puncturing device 1.

The transitional part 35 may have, over the entirety from the proximal end of the transitional part 35 to the distal end of the transitional part 35 or a part thereof, an inner diameter changing so as to have a tapered shape, a stepped shape, a recessed-and-protruding shape, or a wave shape. In particular, the transitional part 35 preferably has, over the entirety from the proximal end to the distal end of the transitional part 35, a diameter decreasing so as to have a tapered shape. If the transitional part 35 has, over the entirety from the proximal end to the distal end thereof, a diameter decreasing so as to have a tapered shape, resistance is less likely to be generated when a liquid having passed through the hole 32 comes into contact with the outer surface of the transitional part 35. Therefore, when the liquid passes through the space between the inner surface of the resin tube 10 and the outer surface of the metal member 30, loss in the pressure of the liquid can be decreased, whereby the flow rate and the flow amount of the liquid to be ejected from the resin tube 10 can be increased.

It is preferable that, as shown in FIG. 7, the large-diameter portion 33 and the transitional part 35 have an inner cavity, and the small-diameter portion 34 has no inner cavity. That is, the inner cavity of the metal member 30 is preferably present on the proximal side relative to the small-diameter portion 34. If the large-diameter portion 33 and the transitional part 35 have an inner cavity, it is possible to increase the flow rate of a liquid in a state of ensuring the flow amount thereof to some extent, in the course of flow of the liquid from the lumen of the metal tube 20 to the hole 32. In addition, if the small-diameter portion 34 has no inner cavity, it is possible to increase the rigidity of the distal end portion, of the resin tube 10, in which the small-diameter portion 34 is present, while ensuring the width of the space between the outer surface of the small-diameter portion 34 and the inner surface of the resin tube 10. As a result, the puncturing device 1 can be configured to: have favorable pushability; easily puncture the fossa ovalis; allow a large amount of liquid such as a physiological saline or a contrast medium to be ejected over a wide range; and provide favorable visibility in intracardiac echocardiography or X-ray irradiation.

It is preferable that, as shown in FIG. 3 and FIG. 7, the opening portion 11 is formed in a surface, of the resin tube 10, perpendicular to the longitudinal direction. If the opening portion 11 is formed on the surface, of the resin tube 10, perpendicular to the longitudinal direction thereof, a liquid inside the flow path 50 can be ejected in a direction along the longitudinal direction of the resin tube 10. That is, a liquid such as a physiological saline or a contrast medium can be ejected toward the distal side or the proximal side, and the liquid can be ejected over a wide range, whereby the visibility in intracardiac echocardiography or X-ray irradiation can be improved.

It is preferable that, as shown in FIG. 3, the opening portion 11 is an opening oriented to the distal side, and a liquid to be ejected from the opening portion 11 is ejected so as to come into contact with the proximal end 40*p* of the metal tip 40. If the liquid to be ejected from the opening portion 11 is ejected so as to come into contact with the proximal end 40*p* of the metal tip 40, a part of the liquid ejected from the opening portion 11 comes into contact with and is rebounded by the proximal end 40*p* of the metal tip 40, whereby the liquid is ejected not only to the distal side but also to the proximal side. As a result, the liquid can be diffused over a further wide range, whereby the visibility in intracardiac echocardiography or X-ray irradiation can be increased. In the case where the proximal end 40*p* of the metal tip 40 is covered with another member such as the resin tube 10 as shown in FIG. 3, a situation in which the liquid ejected from the opening portion 11 comes into indirect contact with the proximal end 40*p* of the metal tip 40 via the other member is also encompassed in the situation in which the liquid ejected from the opening portion 11 comes into contact with the proximal end 40*p* of the metal tip 40.

It is also preferable that, as shown in FIG. 7, the opening portion 11 is an opening oriented to the proximal side. If the opening portion 11 is an opening oriented to the proximal side, a liquid to be ejected from the opening portion 11 can be ejected to the proximal side. Therefore, a liquid such as a physiological saline or a contrast medium can be diffused over a wide range including the proximal side, whereby the visibility in intracardiac echocardiography or X-ray irradiation can be improved.

FIG. 10 is a plan view of a distal end portion of a puncturing device 1 according to still another embodiment of the present invention, FIG. 11 is a cross-sectional view taken along the longitudinal direction of this puncturing device 1, and FIG. 12 and FIG. 13 are cross-sectional views perpendicular to the longitudinal direction of this puncturing device 1. In each of FIG. 10 and FIG. 11, the right side of the drawing is the proximal side, and the left side of the drawing is the distal side.

It is preferable that, as shown in FIG. 10 to FIG. 13, the metal member 30 has a recessed portion 31 extending in the longitudinal direction of the metal member 30. If the metal member 30 has the recessed portion 31 extending in the longitudinal direction, the flow path 50 between the inner surface of the resin tube 10 and the outer surface of the metal member 30 is easily formed, and the cross-sectional area of the flow path 50 can be sufficiently ensured. Therefore, the amount of a liquid to be ejected from the opening portion 11 can be increased.

In a cross section perpendicular to the longitudinal direction, the maximum distance between the recessed portion 31 and the inner surface of the resin tube 10 is preferably not lower than 20%, more preferably not lower than 25%, and further preferably not lower than 30% of the maximum length, of the metal member 30, between two points on the outer periphery of the metal member 30 (hereinafter, sometimes referred to simply as "the maximum length of the metal member 30"). If the lower limit value of the proportion of the maximum distance between the recessed portion 31 and the inner surface of the resin tube 10 to the maximum length of the metal member 30 is set such that the proportion falls within the above range, the cross-sectional area of the flow path 50 in the cross section perpendicular to the longitudinal direction can be ensured, and a sufficient amount of liquid can be caused to flow through the flow path 50. Meanwhile, in the cross section perpendicular to the longitudinal direction, the maximum distance between the recessed portion 31 and the inner surface of the resin tube 10 is preferably not higher than 70%, more preferably not higher than 60%, and further preferably not higher than 50% of the maximum length of the metal member 30. If the upper limit value of the proportion of the maximum distance between the recessed portion 31 and the inner surface of the resin tube 10 to the maximum length of the metal member 30 is set such that the proportion falls within the above range, the strength of the metal member 30 can be maintained, and the rigidity of the distal end portion, of the puncturing device 1, in which the metal member 30 is present can be ensured.

Examples of the cross-sectional shape of the metal member 30 perpendicular to the longitudinal direction include a circular shape, an elliptical shape, a polygonal shape, the shape of a star, the shape of a cross, the shape of the letter H, the shape of the letter U, the shape of a mountain, and a shape obtained by combining these shapes. Further, the cross-sectional shape of the metal member 30 is preferably a shape obtained by providing a cut for forming the flow path 50 to any of these shapes. The cut in the cross-sectional shape corresponds to the recessed portion 31 extending in the longitudinal direction of the metal member 30. In the case of a configuration in which the inner surface of the resin tube 10 and the outer surface of the metal member 30 are partially in close surface contact with each other, the flow path 50 can easily be formed by configuring the metal member 30 to have a cross-sectional shape provided with the cut for forming the flow path 50. In the case of a configuration in which, in the cross section, the inner surface of the resin tube 10 and the outer surface of the metal member 30 are in point contact with each other, the cross-sectional shape of the metal member 30 perpendicular to the longitudinal direction is a shape with vertices such as a polygonal shape or the shape of a star. In the case of a configuration in which the inner surface of the resin tube 10 and the outer surface of the metal member 30 are not in contact with each other, the cross-sectional shape of the metal member 30 perpendicular to the longitudinal direction can be an arbitrarily-set shape.

It is preferable that, as shown in FIG. 12 and FIG. 13, the metal member 30 has a plurality of the recessed portions 31. If the metal member 30 has a plurality of the recessed portions 31, the cross-sectional area of flow paths 50 in the cross section perpendicular to the longitudinal direction can be increased. Consequently, it becomes easy to eject a liquid over a wide range in the diameter direction of the resin tube 10 when the liquid is ejected from the opening portion 11 to the outside.

It is preferable that, as shown in FIG. 4 and FIG. 8, the cross-sectional shape of the metal member 30 perpendicular to the longitudinal direction is a polygonal shape. If the cross-sectional shape of the metal member 30 perpendicular to the longitudinal direction is a polygonal shape, it is possible to, while increasing the cross-sectional area of the flow path 50, maintain the strength of the metal member 30 and maintain the rigidity of the distal end portion, of the puncturing device 1, in which the metal member 30 is present.

The polygonal shape in the present invention encompasses, in addition to polygonal shapes having corners that are definite vertices and having sides that are straight lines, so-called rounded-corner polygonal shapes obtained by rounding the corners of polygons and shapes obtained by curving at least some of the sides of polygons. In the case where a cross section of the metal member 30 perpendicular to the longitudinal direction has a polygonal shape, the vertices of the polygonal shape may be in contact with the inner surface of the resin tube 10 or does not have to be in contact with the inner surface of the resin tube 10. In either of the cases, a material and a hardness of the resin tube 10 are preferably selected so as not to form any portion at which the inner surface of the resin tube 10 is in close contact with the entire circumference of the outer surface of the metal member 30 in the cross section perpendicular to the longitudinal direction. In the case where the cross section of the metal member 30 perpendicular to the longitudinal direction has a polygonal shape, the flow path 50 can be formed between the resin tube 10 and the metal member 30 if the resin tube 10 has a moderate hardness.

Among these shapes, the cross-sectional shape of the metal member 30 perpendicular to the longitudinal direction is more preferably a quadrangular shape. If the cross-sectional shape of the metal member 30 perpendicular to the longitudinal direction is a quadrangular shape, both the strength of the metal member 30 and the size of the flow path 50 can be ensured.

It is preferable that, as shown in FIG. 7 to FIG. 9, the cross-sectional shape of the metal member 30 perpendicular to the longitudinal direction is a circular shape at the large-diameter portion 33 and is a polygonal shape at the small-diameter portion 34. If the cross-sectional shape of the metal member 30 perpendicular to the longitudinal direction is a circular shape at the large-diameter portion 33 and is a polygonal shape at the small-diameter portion 34, the large-diameter portion 33 of the metal member 30 has a shape corresponding to the inner diameter of the metal tube 20 so that the joining strength between the metal member 30 and the metal tube 20 is increased, and furthermore, at the small-diameter portion 34 of the metal member 30, the rigidity of the resin tube 10 is increased while the cross-sectional area of the flow path 50 is ensured, whereby the puncturing device 1 can be configured to have favorable pushability and to easily puncture the fossa ovalis. The small-diameter portion 34 may have a shape obtained by providing a cut for forming the flow path 50 to the aforementioned cross-sectional shape. In the case of a configuration in which the inner surface of the resin tube 10 and the outer surface of the small-diameter portion 34 of the metal member 30 are partially in close surface contact with each other, the flow path 50 can easily be formed by configuring the small-diameter portion 34 to have a cross-sectional shape provided with the cut for forming the flow path 50. In the case of a configuration in which, in the cross section, the inner surface of the resin tube 10 and the outer surface of the small-diameter portion 34 are in point contact with each other, the cross-sectional shape of the small-diameter portion 34 perpendicular to the longitudinal direction of the metal member 30 is a shape with vertices such as a polygonal shape or the shape of a star. In the case of a configuration in which the inner surface of the resin tube 10 and the outer surface of the small-diameter portion 34 are not in contact with each other, the cross-sectional shape of the small-diameter portion 34 perpendicular to the longitudinal direction of the metal member 30 can be an arbitrarily-set shape.

It is preferable that, as shown in FIG. 8 and FIG. 12, the cross-sectional area of the metal member 30 is larger than the cross-sectional area of the flow path 50 in a cross section perpendicular to the longitudinal direction of the metal member 30. If the cross-sectional area of the metal member 30 is larger than the cross-sectional area of the flow path 50, the rigidity of a part, of the distal end portion of the puncturing device 1, in which the metal member 30 is present can be increased. Therefore, the insertability of the puncturing device 1 is increased.

In the cross section perpendicular to the longitudinal direction of the metal member 30, the cross-sectional area of the metal member 30 is preferably not lower than 1.1 times, more preferably not lower than 1.3 times, and further preferably not lower than 1.5 times the cross-sectional area of the flow path 50. If the lower limit value of the ratio of the cross-sectional area of the metal member 30 to the cross-sectional area of the flow path 50 is set such that the ratio falls within the above range, the rigidity of the distal end portion, of the puncturing device 1, in which the metal member 30 is disposed can be sufficiently increased. Meanwhile, the cross-sectional area of the metal member 30 is preferably not higher than 5 times, more preferably not higher than 4 times, and further preferably not higher than 3 times the cross-sectional area of the flow path 50. If the upper limit value of the ratio of the cross-sectional area of the metal member 30 to the cross-sectional area of the flow path 50 is set such that the ratio falls within the above range, it is possible to prevent excessive increase in the outer diameter of the distal end portion of the puncturing device 1 while ensuring the cross-sectional area of the flow path 50.

It is preferable that, as shown in FIG. 3, FIG. 4, FIG. 11, and FIG. 12, the metal member 30 has a portion at which the outer surface of the metal member 30 is at least partially in contact with the inner surface of the resin tube 10. If the metal member 30 has the portion at which the outer surface of the metal member 30 is at least partially in contact with the inner surface of the resin tube 10, the rigidity of the distal end portion, of the puncturing device 1, in which the metal member 30 is present can be increased by the metal member 30, whereby the puncturing device 1 can be configured to have favorable insertability.

It is preferable that, in a section in which the flow path 50 is present, the outer surface of the metal member 30 is partially in contact with the inner surface of the resin tube 10 along the longitudinal direction. A portion at which the outer surface of the metal member 30 and the inner surface of the resin tube 10 are not in contact with each other is the flow path 50, and the portion at which said outer surface and said inner surface are in contact with each other is a portion for maintaining the strength of the distal end portion of the puncturing device 1.

In the case where the outer surface of the metal member 30 is at least partially in contact with the inner surface of the resin tube 10, it is preferable that, as shown in FIG. 12, the metal member 30 is in surface contact with the inner surface of the resin tube 10 at a plurality of locations in the cross section perpendicular to the longitudinal direction of the metal member 30. If the metal member 30 is in surface contact with the inner surface of the resin tube 10 at a plurality of locations, a plurality of the flow paths 50 are present. Consequently, it becomes easy to eject a liquid over a wide range in the diameter direction of the resin tube 10 when the liquid is ejected from the opening portion 11 to the outside.

In the cross section perpendicular to the longitudinal direction of the metal member 30, the length over which the metal member 30 is in surface contact with the inner surface of the resin tube 10 is preferably not lower than 10%, more preferably not lower than 20%, and further preferably not lower than 30% of the length of the outer surface of the metal member 30. If the lower limit value of the proportion of the length over which the metal member 30 is in surface contact with the inner surface of the resin tube 10 to the length of the outer surface of the metal member 30 is set such that the proportion falls within the above range, the length of the portion at which the resin tube 10 and the metal member 30 are in contact with each other in the cross section perpendicular to the longitudinal direction can be made sufficient. As a result, a liquid sent into the flow path 50 can be prevented from flowing between the resin tube 10 and the metal member 30 at a portion that is not the flow path 50, and the amount of the liquid to be ejected from the distal end 10d of the resin tube 10 can be ensured. Meanwhile, in the cross section perpendicular to the longitudinal direction of the metal member 30, the length over which the metal member 30 is in surface contact with the inner surface of the resin tube 10 is preferably not higher than 50%, more preferably not higher than 45%, and further preferably not higher than 40% of the length of the outer surface of the metal member 30. If the upper limit value of the proportion of the length over which the metal member 30 is in surface contact with the inner surface of the resin tube 10 to the length of the outer surface of the metal member 30 is set such that the proportion falls within the above range, the cross-sectional area of the flow path 50 in the cross section perpendicular to the longitudinal direction can be increased, and the amount of the liquid to be ejected from the distal end 10d of the resin tube 10 can be increased.

It is also preferable that, as shown in FIG. 7 and FIG. 8, the metal member 30 has, on the distal side relative to the distal end 20d of the metal tube 20, no portion in contact with the inner surface of the resin tube 10. If the metal member 30 has, on the distal side relative to the distal end 20d of the metal tube 20, no portion in contact with the inner surface of the resin tube 10, the flow path 50 can be ensured, and the flow amount of a liquid to pass through the flow path 50 can be increased by increasing the size of the flow path 50.

It is preferable that, as shown in FIG. 9, the metal member 30 is in surface contact with the inner surface of the metal tube 20. If the metal member 30 is in surface contact with the inner surface of the metal tube 20, the surface area over which the metal tube 20 and the metal member 30 are in contact with each other can be increased. Therefore, the joining strength between the metal tube 20 and the metal member 30 can be increased, and the metal member 30 can be made less likely to be detached from the metal tube 20 even in a state where the puncturing device 1 is inserted into a curved lumen inside the body. In the cross section perpendicular to the longitudinal direction of the metal member 30, the length over which the metal member 30 is in surface contact with the inner surface of the metal tube 20 can be selected in consideration of the joining strength between the metal tube 20 and the metal member 30 and the flow amount in the flow path 50.

It is preferable that, as shown in FIG. 2, FIG. 3, FIG. 6, FIG. 7, FIG. 10, and FIG. 11, the resin tube 10 has, on the proximal side relative to the proximal end 40p of the metal tip 40, an opposed surface 14 opposed to the opening portion 11. If the resin tube 10 has the opposed surface 14, it becomes easy for a liquid that had been inside the flow path 50 and that has been ejected from the opening portion 11 to come into contact with the opposed surface 14. The liquid having come into contact with the opposed surface 14 is rebounded. Consequently, the liquid can be ejected over a wide range, whereby the visibility in intracardiac echocardiography or X-ray irradiation can be increased.

It is preferable that, as shown in FIG. 2 and FIG. 3, the resin tube 10 has, on the proximal side relative to the opposed surface 14, a narrowed portion 15 having an outer diameter smaller than the outer diameter of the resin tube 10 on the proximal side relative to the opening portion 11. If the resin tube 10 has the narrowed portion 15, it becomes easy for a liquid that had been inside the flow path 50 and that has been ejected from the opening portion 11 to come into contact with the opposed surface 14, and much of the liquid is rebounded by the opposed surface 14, whereby the liquid can be diffused over a wide range. As a result, the visibility in intracardiac echocardiography or X-ray irradiation can be improved.

The minimum outer diameter of the narrowed portion 15 is preferably not higher than 0.8 times, more preferably not higher than 0.7 times, and further preferably not higher than 0.6 times the maximum outer diameter of the resin tube 10 on the proximal side relative to the opening portion 11. If the upper limit value of the ratio of the minimum outer diameter of the narrowed portion 15 to the maximum outer diameter of the resin tube 10 on the proximal side relative to the opening portion 11 is set such that the ratio falls within the above range, it becomes easy for a liquid that had been inside the flow path 50 and that has been ejected from the opening portion 11 to be ejected toward the opposed surface 14 without being blocked by the narrowed portion 15. Meanwhile, the minimum outer diameter of the narrowed portion 15 is preferably not lower than 0.2 times, more preferably not lower than 0.25 times, and further preferably not lower than 0.3 times the maximum outer diameter of the resin tube 10 on the proximal side relative to the opening portion 11. If the lower limit value of the ratio of the minimum outer diameter of the narrowed portion 15 to the maximum outer diameter of the resin tube 10 on the proximal side relative to the opening portion 11 is set such that the ratio falls within the above range, the strength of the narrowed portion 15 can be sufficiently maintained, and the durability of the distal end portion of the puncturing device 1 can be made sufficient.

It is preferable that, as shown in FIG. 3, the resin tube 10 has a contact portion 16 in contact with the metal member 30, and the opening portion 11 is present on the proximal side relative to the contact portion 16. Since the contact portion 16 is a portion, of the resin tube 10, that is in contact with the metal member 30, the outer diameter of the contact portion 16 is smaller than that of the other portion of the resin tube 10. Therefore, since the opening portion 11 is present on the proximal side relative to the contact portion 16, when a liquid inside the flow path 50 is ejected from the opening portion 11, the liquid heading for the distal side is less likely to come into contact with the contact portion 16, and the liquid can be ejected over a wide range. As a result, the puncturing device 1 can be configured to provide a high visibility in intracardiac echocardiography or X-ray irradiation.

It is also preferable that, as shown in FIG. 11, the resin tube 10 has the contact portion 16 in contact with the metal member 30, and the opening portion 11 is present on the distal side relative to the contact portion 16. If the opening portion 11 is present on the distal side relative to the contact portion 16, when a liquid inside the flow path 50 is ejected from the opening portion 11, the liquid heading for the proximal side is less likely to come into contact with the contact portion 16, and the liquid can be ejected over a wide range, whereby the visibility in intracardiac echocardiography or X-ray irradiation can be improved.

FIG. 14 is an enlarged view of a distal end portion of a puncturing device 1 according to a different embodiment of the present invention, and FIG. 15 is an enlarged view of a distal end portion of a puncturing device 1 according to a still different embodiment of the present invention. In each of FIG. 14 and FIG. 15, the right side of the drawing is the proximal side, and the left side of the drawing is the distal side.

It is preferable that, as shown in FIG. 14, the resin tube 10 has, on the proximal side relative to the opposed surface 14, a narrowed portion 15 having an outer diameter smaller than the outer diameter of the resin tube 10 on the proximal side relative to the opening portion 11, and the narrowed portion 15 has a diameter-decreasing portion 15a having an outer diameter decreasing from the proximal side toward the distal side. If the narrowed portion 15 has the diameter-decreasing portion 15a, more of a liquid that had been inside the flow path 50 and that has been ejected from the opening portion 11 flows toward the opposed surface 14, and the liquid is rebounded by the opposed surface 14 and diffused to the proximal side. As a result, the liquid such as a physiological saline or a contrast medium can be ejected over a wide range, whereby the visibility in intracardiac echocardiography or X-ray irradiation can be increased.

The diameter-decreasing portion 15a may be the entirety or a portion, of the narrowed portion 15, that has an outer diameter decreasing from the proximal side toward the distal side so as to have a tapered shape, a stepped shape, a recessed-and-protruding shape, or a wave shape. In particular, it is preferable that the diameter-decreasing portion 15a is the entirety, of the narrowed portion 15, that has a diameter decreasing from the proximal end toward the distal end of the narrowed portion 15 so as to have a tapered shape. If the diameter-decreasing portion 15a is the entirety, of the narrowed portion 15, that has a diameter decreasing from the proximal end toward the distal end of the narrowed portion 15 so as to have a tapered shape, much of a liquid ejected from the opening portion 11 easily comes into contact with the opposed surface 14, and more of the liquid can be diffused over a wide range, whereby the visibility in intracardiac echocardiography or X-ray irradiation can be improved.

It is also preferable that, as shown in FIG. 15, the resin tube 10 has, on the proximal side relative to the opposed surface 14, a narrowed portion 15 having an outer diameter smaller than the outer diameter of the resin tube 10 on the proximal side relative to the opening portion 11, and the narrowed portion 15 has a diameter-increasing portion 15b having an outer diameter increasing from the proximal side toward the distal side. If the narrowed portion 15 has the diameter-increasing portion 15b, the size of the opening portion 11 can be increased, whereby the amount of a liquid inside the flow path 50 to be ejected from the opening portion 11 can be increased. Therefore, a large amount of the liquid such as a physiological saline or a contrast medium can be ejected from the opening portion 11, whereby the visibility in intracardiac echocardiography or X-ray irradiation can be increased.

The diameter-increasing portion 15b may be the entirety or a portion, of the narrowed portion 15, that has an outer diameter increasing from the proximal side toward the distal side so as to have a tapered shape, a stepped shape, a recessed-and-protruding shape, or a wave shape. In particular, it is preferable that the diameter-increasing portion 15b is the entirety, of the narrowed portion 15, that has a diameter increasing from the proximal end toward the distal end of the narrowed portion 15 so as to have a tapered shape.

If the diameter-increasing portion 15*b* is the entirety, of the narrowed portion 15, that has a diameter increasing from the proximal end toward the distal end of the narrowed portion 15 so as to have a tapered shape, it is possible to sufficiently ensure also the size of the opposed surface 14 while increasing the size of the opening portion 11, and a liquid ejected from the opening portion 11 can be rebounded by the opposed surface 14 and can be diffused over a wide range, whereby the visibility in intracardiac echocardiography or X-ray irradiation can be improved.

The narrowed portion 15 may have only one of the diameter-decreasing portion 15*a* and the diameter-increasing portion 15*b*, or may have both the diameter-decreasing portion 15*a* and the diameter-increasing portion 15*b*. In the case where the narrowed portion 15 has both the diameter-decreasing portion 15*a* and the diameter-increasing portion 15*b*, the diameter-decreasing portion 15*a* is preferably present on the proximal side relative to the diameter-increasing portion 15*b*. If the narrowed portion 15 has the diameter-decreasing portion 15*a* and the diameter-increasing portion 15*b* on the distal side relative to the diameter-decreasing portion 15*a*, a liquid that had been inside the flow path 50 and that has been ejected from the opening portion 11 heads for the distal side along the diameter-decreasing portion 15*a*, and a part of the liquid is returned to the proximal side by the diameter-increasing portion 15*b*. Therefore, a part of the liquid ejected from the opening portion 11 heads for the distal side, and another part of the liquid heads for the proximal side, whereby the liquid can be diffused over a wide range. As a result, the visibility in intracardiac echocardiography or X-ray irradiation can be increased.

Although not shown, it is preferable that the metal tip 40 has an inner cavity, and an X-ray opaque marker is disposed inside the metal tip 40. If the X-ray opaque marker is disposed in the inner cavity of the metal tip 40, the imaging performance, for X rays, of the metal tip 40 can be increased. Therefore, if X rays are used during use of the puncturing device 1, it becomes easy to check the position of the metal tip 40 inside the body.

As a material from which the X-ray opaque marker is made, it is possible to use, for example, an X-ray opaque substance such as lead, barium, iodine, tungsten, gold, platinum, iridium, a platinum-iridium alloy, stainless steel, titanium, palladium, or a cobalt-chromium alloy. Among these substances, the X-ray opaque substance is preferably a platinum-iridium alloy. If the material from which the X-ray opaque marker is made is a platinum-iridium alloy, the imaging performance for X rays can be increased, whereby it becomes easy to check the position of the metal tip 40 through X-ray irradiation.

Examples of the shape of the X-ray opaque marker include a spherical shape, a cylindrical shape, a polygonal tubular shape, a shape having a C-shaped cross section and obtained by forming a slit in a tube, a coil shape obtained by winding a wire material, a columnar shape, and a polygonal prism shape. The X-ray opaque marker may be disposed at a location other than the location in the inner cavity of the metal tip 40. The number of the X-ray opaque markers may be one or may be two or more.

It is preferable that, as shown in FIG. 7, the resin tube 10 has a reinforcing member 13 on the distal side relative to the distal end 20*d* of the metal tube 20. If the resin tube 10 has the reinforcing member 13 on the distal side relative to the distal end 20*d* of the metal tube 20, the distal end portion of the resin tube 10 is reinforced by the reinforcing member 13 and comes to have an increased rigidity. Therefore, the puncturing device 1 can be configured to have favorable pushability and to easily puncture the fossa ovalis.

The reinforcing member 13 may be, for example, formed in the shape of a layer of tubular member or the like or obtained by arranging or braiding, in a specific pattern, wire materials that are each a single wire or a twisted wire. The reinforcing member 13 can be disposed on the outer surface of a circumferential wall of the resin tube 10 or the inner surface of said circumferential wall, or inside said circumferential wall.

Examples of a material from which the reinforcing member 13 is made include: metals such as stainless steel, titanium, nickel-titanium alloys, cobalt-chromium alloys, and tungsten alloys; and synthetic resins such as polyarylate-based resins, aramid-based resins, and polyolefin-based resins such as ultrahigh-molecular-weight polyethylene. The reinforcing member 13 may be made from one type of material or may contain a plurality of types of materials.

It is preferable that the reinforcing member 13 is a metal tubular member, and, as shown in FIG. 7, the reinforcing member 13 is disposed on the inner surface of the resin tube 10. If the reinforcing member 13 is a metal tubular member and is disposed on the inner surface of the resin tube 10, it is possible to, while increasing the rigidity of the entire distal end portion of the resin tube 10, smooth the surface of the distal end portion of the resin tube 10 so as to improve the slidability of the resin tube 10. In the case where the reinforcing member 13 which is a tubular member is disposed on the inner surface of the resin tube 10, the flow path 50 is present between the outer surface of the metal member 30 and the inner surface of the reinforcing member 13 of the resin tube 10.

As described above, the puncturing device according to the present invention includes: a resin tube having a distal end and a proximal end, and extending in a longitudinal direction; a metal tube disposed in a lumen of the resin tube; a metal member disposed at a distal end portion of the metal tube; and a metal tip disposed at a distal end portion of the metal member. The resin tube includes a flow path which is present between an inner surface of the resin tube and an outer surface of the metal member and which is in communication with a lumen of the metal tube, the distal end of the resin tube is present between a distal end and a proximal end of the metal tip, the resin tube further includes an opening portion through which the flow path and outside of the resin tube are in communication with each other, and the opening portion is present on a distal side relative to a distal end of the metal tube and on a proximal side relative to the proximal end of the metal tip. Since the puncturing device according to the present invention has such a configuration, it is possible to increase the width of the flow path and the size of the opening portion while maintaining the rigidity of the distal end portion of the puncturing device for the insertability of the puncturing device into a lumen, inside a living body, of a blood vessel or the like and ease of puncturing of the fossa ovalis by the puncturing device. Therefore, a liquid such as a physiological saline or a contrast medium can be ejected over a wide range inside the left atrium, whereby the visibility in intracardiac echocardiography or X-ray irradiation can be increased.

This application claims priority to Japanese Patent Application No. 2021-025788, filed on Feb. 22, 2021. All of the contents of the Japanese Patent Application No. 2021-025788, filed on Feb. 22, 2021, are incorporated by reference herein.

REFERENCE SIGNS LIST

1: puncturing device
2: shaft
3: handle
4: syringe port
5: cable
6: connector
10: resin tube
10*d*: distal end of the resin tube
11: opening portion
12: bent portion
13: reinforcing member
14: opposed surface
15: narrowed portion
15*a*: diameter-decreasing portion
15*b*: diameter-increasing portion
16: contact portion
20: metal tube
20*d*: distal end of the metal tube
30: metal member
30*p*: proximal end of the metal member
31: recessed portion
32: hole
33: large-diameter portion
34: small-diameter portion
35: transitional part
40: metal tip
40*d*: distal end of the metal tip
40*p*: proximal end of the metal tip
41: opposed surface
50: flow path

The invention claimed is:

1. A puncturing device comprising:
a resin tube having a distal end and a proximal end, and extending in a longitudinal direction;
a metal tube disposed in a lumen of the resin tube;
a metal member disposed at a distal end portion of the metal tube; and
a metal tip disposed at a distal end portion of the metal member, wherein
the resin tube includes a flow path which is present between an inner surface of the resin tube and an outer surface of the metal member and which is in communication with a lumen of the metal tube,
the resin tube further includes an opening portion through which the flow path and outside of the resin tube are in communication with each other,
the opening portion is present on a distal side relative to a distal end of the metal tube and on a proximal side relative to a proximal end of the metal tip,
the metal member has an inner cavity opened to at least the proximal side,
the metal member includes a large-diameter portion and a small-diameter portion which is located on the distal side relative to the large-diameter portion and which has a smaller outer diameter than the large-diameter portion, and
the metal member further includes a hole, so that the lumen of the metal tube and a space between the inner surface of the resin tube and the outer surface of the metal member are in communication with each other through the hole of the metal member.

2. The puncturing device according to claim 1, wherein the opening portion is formed in a plane, of the resin tube, perpendicular to the longitudinal direction.

3. The puncturing device according to claim 1, wherein the resin tube is configured so that the opening portion faces to the distal side, and a fluid is ejected from the opening portion toward the distal side.

4. The puncturing device according to claim 1, wherein the resin tube is configured so that the opening portion faces to the proximal side and a fluid is ejected from the opening portion toward the proximal side.

5. The puncturing device according to claim 1, wherein the outer surface of the metal member has a recessed portion extending in a longitudinal direction of the metal member to form the flow pass.

6. The puncturing device according to claim 1, wherein a cross-sectional shape of the metal member perpendicular to the longitudinal direction is a polygonal shape.

7. The puncturing device according to claim 1, wherein a cross-sectional area of the metal member is larger than a cross-sectional area of the flow path in a cross section perpendicular to a longitudinal direction of the metal member.

8. The puncturing device according to claim 1, wherein the outer surface of the metal member is at least partially in contact with the inner surface of the resin tube.

9. The puncturing device according to claim 1, wherein the metal member has, on the distal side relative to the distal end of the metal tube, no portion in contact with the inner surface of the resin tube.

10. The puncturing device according to claim 1, wherein the resin tube has a contact portion in contact with the metal member, and
the opening portion is present on the proximal side relative to the contact portion.

11. The puncturing device according to claim 1, wherein the resin tube has a contact portion in contact with the metal member, and
the opening portion is present on the distal side relative to the contact portion.

12. The puncturing device according to claim 1, wherein the resin tube has, on the proximal side relative to an opposed surface opposed to the opening portion, a narrowed portion having an outer diameter smaller than an outer diameter of the resin tube on the proximal side relative to the opening portion, and
the narrowed portion has a diameter-decreasing portion having an outer diameter decreasing from the proximal side toward the distal side.

13. The puncturing device according to claim 1, wherein the resin tube has, on the proximal side relative to an opposed surface opposed to the opening portion, a narrowed portion having an outer diameter smaller than an outer diameter of the resin tube on the proximal side relative to the opening portion, and
the narrowed portion has a diameter-increasing portion having an outer diameter increasing from the proximal side toward the distal side.

14. The puncturing device according to claim 1, wherein the resin tube has a reinforcing member on the distal side relative to the distal end of the metal tube.

15. The puncturing device according to claim 14, wherein the reinforcing member is a metal tubular member, and the reinforcing member is disposed on the inner surface of the resin tube.

16. The puncturing device according to claim 1, wherein the distal end of the resin tube is present between a distal end and the proximal end of the metal tip.

17. A puncturing device, comprising:

a resin tube having a distal end and a proximal end, and extending in a longitudinal direction;

a metal tube disposed in a lumen of the resin tube;

a metal member disposed at a distal end portion of the metal tube; and a metal tip disposed at a distal end portion of the metal member, wherein the resin tube includes a flow path which is present between an inner surface of the resin tube and an outer surface of the metal member and which is in communication with a lumen of the metal tube, the resin tube further includes an opening portion through which the flow path and outside of the resin tube are in communication with each other, the opening portion is present on a distal side relative to a distal end of the metal tube and on a proximal side relative to a proximal end of the metal tip, the resin tube has, on the proximal side relative to the proximal end of the metal tip, an opposed surface opposed to the opening portion, and the resin tube has, on the proximal side relative to the opposed surface, a narrowed portion having an outer diameter smaller than an outer diameter of the resin tube on the proximal side relative to the opening portion.

\* \* \* \* \*